(12) United States Patent
Cordelier et al.

(10) Patent No.: US 10,760,135 B2
(45) Date of Patent: Sep. 1, 2020

(54) METHODS FOR PREDICTING PANCREATIC CANCER TREATMENT RESPONSE

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); CENTRE HOSPITALIER UNIVERSITAIRE DE TOULOUSE, Toulouse (FR)

(72) Inventors: Pierre Cordelier, Toulouse (FR); Louis Buscail, Toulouse (FR); Frédéric Lopez, Toulouse (FR)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 124 days.

(21) Appl. No.: 16/068,772

(22) PCT Filed: Jan. 13, 2016

(86) PCT No.: PCT/IB2016/000099
§ 371 (c)(1),
(2) Date: Jul. 9, 2018

(87) PCT Pub. No.: WO2017/122039
PCT Pub. Date: Jul. 20, 2017

(65) Prior Publication Data
US 2019/0024186 A1    Jan. 24, 2019

(51) Int. Cl.
*C07H 21/04* (2006.01)
*C12Q 1/6886* (2018.01)
*G01N 33/574* (2006.01)
*A61P 35/00* (2006.01)
*A61K 31/7068* (2006.01)
*A61K 48/00* (2006.01)

(52) U.S. Cl.
CPC ........ *C12Q 1/6886* (2013.01); *A61K 31/7068* (2013.01); *A61K 48/00* (2013.01); *A61P 35/00* (2018.01); *G01N 33/57438* (2013.01); *C12Q 2600/106* (2013.01); *C12Q 2600/158* (2013.01); *C12Q 2600/178* (2013.01); *G01N 2800/52* (2013.01)

(58) Field of Classification Search
None
See application file for complete search history.

(56) References Cited

FOREIGN PATENT DOCUMENTS

| EP | 2 047 858 A1 | 4/2009 |
| WO | 2014/198995 A1 | 12/2014 |

OTHER PUBLICATIONS

Park, Jong-Kook, et al. "Antisense inhibition of microRNA-21 or-221 arrests cell cycle, induces apoptosis, and sensitizes the effects of gemcitabine in pancreatic adenocarcinoma." Pancreas 38.7 (2009): e190-e199.*
Wang, Jin, et al. "MicroRNAs in plasma of pancreatic ductal adenocarcinoma patients as novel blood-based biomarkers of disease." Cancer prevention research 2.9 (2009): 807-813.*
Buscail et al., "First-in-man Phase 1 Clinical Trial of Gene Therapy for Advanced Pancreatic Cancer: Safety, Biodistribution, and Preliminary Clinical Findings", Molecular Therapy, Jan. 14, 2015, pp. 779-789, vol. 23, No. 4.

* cited by examiner

*Primary Examiner* — Kimberly Chong
(74) *Attorney, Agent, or Firm* — W&C IP

(57) ABSTRACT

The present invention relates to methods for predicting pancreatic cancer treatment response.

2 Claims, 9 Drawing Sheets

Figure 1A:
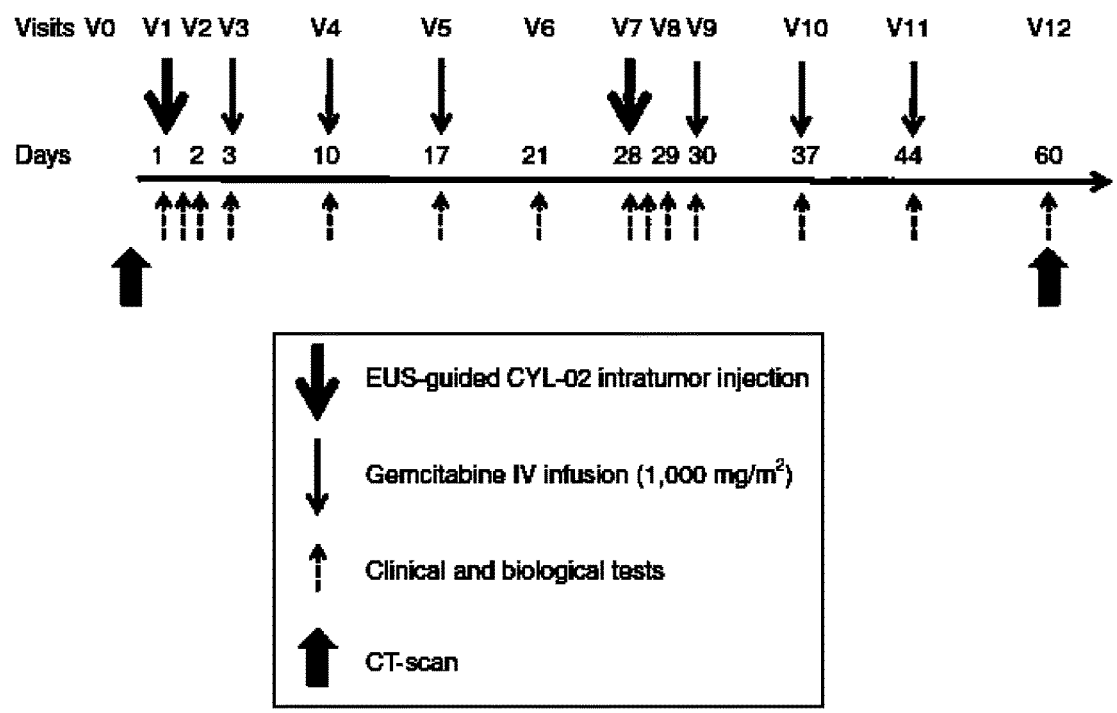

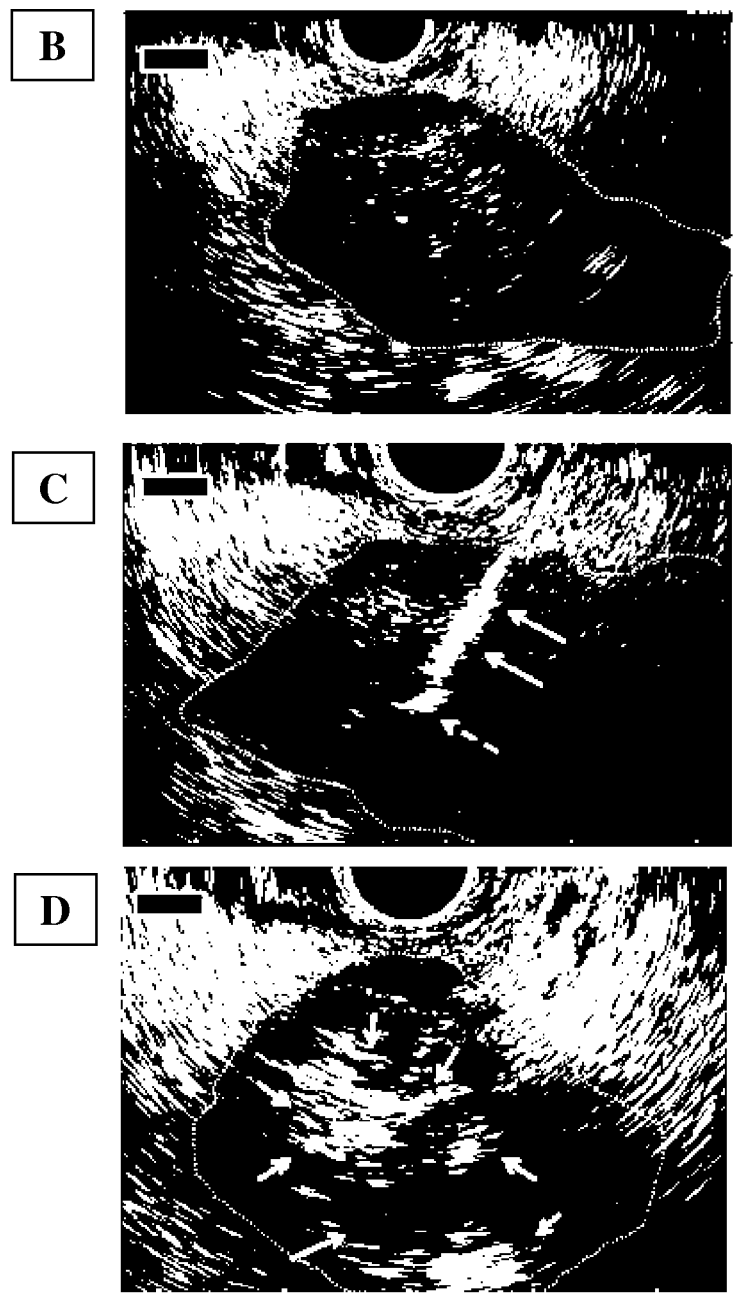
Figure 1 B, C and D

METHODS FOR PREDICTING PANCREATIC CANCER TREATMENT RESPONSE

FIELD OF THE INVENTION

The present invention relates to methods for predicting pancreatic cancer treatment response.

BACKGROUND OF THE INVENTION

Pancreatic ductal adenocarcinoma (PDAC) is the fourth leading cause of cancer death in Western countries, with the lowest five-year relative (1) and 1-year survival rates (2) among commonly diagnosed cancers. PDAC is anticipated to move to the second leading cause of cancer death worldwide by 2020 in the absence of improvements in early detection and/or treatment (3).

Since 1997, Gemcitabine is the only approved first-line treatment for patients with advanced PDAC (2); however, the 5-year survival rate is only 2% (1), with 1-year survival rates ranging from 17 to 23% (2). Recently, phase II and III trials exploring gemcitabine-based combinations with erlotinib (4) or nab-Paclitaxel (5) were found to improve overall survival of patients with a metastatic disease. Thus, the moderate activity of standard gemcitabine and gemcitabine-based regimens strongly encourages new therapeutic research programs such as gene therapy.

The inventors devised in the past decade a highly innovative approach based on therapeutic gene transfer using non-viral vectors to restore SSTR2 expression (encoding for somatostatin receptor subtype 2) that is lost in 95% of PDAC tumors (6). The inventors found that SSTR2-based gene therapy induces a strong bystander antitumoral effect that is antiproliferative, pro-apoptotic, anti-angiogenic, and anti-metastatic (7-12). Resistance to gemcitabine is a major cause of unsatisfactory improvement during pancreatic cancer treatment may help identify novel therapeutic target genes to enhance the efficacy of gemcitabine treatment. DeoxyCytidine Kinase (DCK) phosphorylates gemcitabine to gemcitabine diphosphate in a rate-limiting step. Loss of expression of this key enzyme was recently associated with acquired resistance to gemcitabine in pancreatic cancer cells, in preclinical models (13), and in patients (14). The inventors demonstrated that delivering DCK::UMK fusion gene, encoding for both DCK and Uridylate Monophosphate Kinase (UMK), using non-viral vectors overcomes PDAC-derived cells resistance to gemcitabine (15). Thus, as opposed to many trials for PDAC treatment in which new agents are combined with gemcitabine simply because it is a standard of care, there is a strong rationale to deliver DCK and UMK genes and to treat advanced pancreatic cancer tumors with chemotherapy.

The phase I study was conducted to determine the recommended phase two dose (RPTD) of a clinical-grade, gene therapy product combining for the first time SSTR2, DCK and UMK gene expression, delivered by a non-viral vector, and administered with gemcitabine in patients with advanced pancreatic cancer. The inventors characterized the feasibility, tolerability and toxicity profile of the regimen and examined preliminary efficacy. Pharmacokinetic and biomarker studies were also performed.

Taking into account the risk of these treatments, the increasing number of available therapeutic molecules in pancreatic cancer, the variability of the response to the various treatment, and to optimize the drug prescription, identification of predictive markers of gene therapy and gemcitabine combination may be highly desirable.

SUMMARY OF THE INVENTION

The present invention relates to methods for determining whether a subject afflicted with pancreatic cancer will be a responder or a non-responder to a gene therapy and gemcitabine combination treatment.

DETAILED DESCRIPTION OF THE INVENTION

The inventors performed high-throughput proteomic studies from the plasma of patients diagnosed with locally advanced PDAC, before treatment by gene therapy. Proteomic data successfully classified patients with locally advanced tumors in two groups, high responders and low responders, to gene therapy. The inventors validated that statistical analysis of differences between groups was strictly related to biological parameters. The inventors identified a set of 25 proteins with a significant Mascot score, that discriminate the two groups of patients and validated that A2MG (α2-macroglobuline) is elevated prior to treatment in patients that will better respond to gene therapy. The inventors also identified a set of 9 polypeptides (A2MG, K2C1, APOA1, EXOC2, TRFE, CO5, A16L2, FBLN3 and VTNC) and a set of 12 miRNAs (miR-378, miR-145, miR-150, miR-185, miR-21, miR-484, miR-625, miR-122, miR-320, miR-335, miR-365 and miR-342-3p), that are significantly elevated in the plasma of high responders to treatment and a set of 16 polypeptides (IGHG4, FIBG, AACT, HRG, KING1, FETUA, PLMN, THRB, KLBK1, APOH, FHR5, M3K19, CLUS, PROS, C4BP4 and FIBB) that are significantly decreased in the plasma of high responders to treatment.

Methods for Predicting Response

Accordingly, the present invention relates to a method of determining whether a subject afflicted with pancreatic cancer will be a responder or a non-responder to a gene therapy and gemcitabine combination treatment comprising the step of measuring the expression level of at least one biomarker selected from A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p in a blood sample obtained from said subject before the treatment.

Typically, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 biomarker selected from the group consisting of A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p are measured.

The term "subject" denotes a mammal. In a preferred embodiment of the invention, a subject refers to any subject (preferably human) afflicted with pancreatic cancer. In another preferred embodiment of the invention, the term "subject" refers to any subject (preferably human) afflicted with Pancreatic ductal adenocarcinoma (PDAC). In another preferred embodiment of the invention, the term "subject" refers to any subject (preferably human) afflicted with Pancreatic ductal adenocarcinoma (PDAC) receiving a gemcitabine first-line therapy.

The term "pancreatic cancer" refers to pancreatic cancer such as revised in the World Health Organisation Classification C25. The term "pancreatic cancer" also refers to Pancreatic ductal adenocarcinoma (PDAC) (31-35). The term "pancreatic cancer" also refers to metastatic pancreatic cancer, exocrine pancreatic cancer and locally advanced PDAC.

The term "gene therapy" denotes the therapeutic gene transfer using expression vector coding for at least one gene selected from the group consisting of SSTR2, DCK and UMK to restore gene expression. The term "gene therapy" also refers to therapeutic gene transfer using non-viral vectors to restore expression of at least one gene selected from the group consisting of SSTR2, DCK and UMK such as described in WO 2009/056434. In a preferred embodiment of the invention, the term "gene therapy" refers to delivering DCK::UMK fusion gene, encoding for both DCK and UMK, using for example non-viral vectors.

The term "SSTR2" has its general meaning in the art and refers to somatostatin receptor subtype 2 such as described in WO 2009/056434.

The term "DCK" has its general meaning in the art and refers to DeoxyCytidine Kinase such as described in WO 2009/056434.

The term "UMK" has its general meaning in the art and refers to Uridylate Monophosphate Kinase such as described in WO 2009/056434.

The term "gemcitabine" has its general meaning in the art and refers to Gemcitabine HCl/Chlorhydrate, marketed by Eli Lilly under the trademark Gemzar®, which is a nucleoside analogue that exhibits antitumor activity and belongs to a general group of chemotherapy drugs known as antimetabolites. Gemcitabine prevents cells from producing DNA and RNA by interfering with the synthesis of nucleic acids, thus stopping the growth of cancer cells and causing them to die. The term "gemcitabine" also refers to synthetic glucoside analog of cytosine, which is chemically described as 1-(2'-Deoxy-2',2'-difluoro-[beta]-D-ribofuranosyl)-4-aminopyrimidin-2-one hydrochloride or 2'-deoxy-2',2'-difluorocytidine monohydrochloride [beta] isomer) such as described in the International publication No. WO 97/21719.

The term "Alpha-2-macroglobulin" also known as A2M, A2MG and α2M has its general meaning in the art and refers to the glycoprotein A2M such as described in Borth W. Alpha 2-macroglobulin, a multifunctional binding protein with targeting characteristics. FASEB J. 1992 December; 6(15):3345-53; Borth W. Alpha 2-macroglobulin. A multifunctional binding and targeting protein with possible roles in immunity and autoimmunity. Ann N Y Acad Sci. 1994 Sep. 10; 737:267-72.

As used herein, the term "miR" has its general meaning in the art and refers to the miRNA sequence publicly available from the data base http://microrna.sanger.ac.uk/sequences/under the miRBase Accession number.

All the polypeptide and miRNA biomarkers pertaining to the invention are known per se, and are listed in the below Tables A and B.

TABLE A list of the polypeptide biomarkers according to the invention

| Polypeptide symbol | Polypeptides name | Accession number |
|---|---|---|
| A2MG | Alpha-2-macroglobulin | P01023 |
| K2C1 | Keratin, type II cytoskeletal 1 | P04264 |
| APOA1 | Apolipoprotein A-1 | P02647 |
| EXOC2 | Exocyst complex component 2 | Q96KPI |
| TRFE | Serotransferrin | P02787 |
| CO5 | Complement C5 | P01031 |
| A16L2 | Autophagy-related protein 16-2 | Q8NAA4 |
| FBLN3 | EGF-containing fibulin-like extracellular matrix protein 1 | Q12805 |
| VTNC | Vitronectin | P04004 |
| IGHG4 | Ig gamma-4 chain C region | P01861 |
| FIBG | Fibrinogen gamma chain | P02679 |
| AACT | Alpha-1-antichymotrypsin | P01011 |
| HRG | Histidine-rich glycoprotein | P04196 |
| KING1 | | |
| FETUA | Alpha-2-HS-glycoprotein | P02765 |
| PLMN | Plasminogen | P00747 |
| THRB | Thyroid hormone receptor beta | P10828 |
| KLBK1 | | |
| APOH | Apolipoprotein H, beta-2-glycoprotein 1 | P02749 |
| FHR5 | Complement factor H-related protein 5 | Q9BXR6 |
| M3K19 | Mitogen-Activated Protein Kinase 19 | Q56UN5 |
| CLUS | Clusterin | P10909 |
| PROS | Vitamin K-dependent protein S | P07225 |
| C4BP4 | Complement component 4 binding protein 4 | P04003 |
| FIBB | Fibrinogen beta chain | P02675 |

TABLE B list of the miRNAs biomarkers according to the invention

| miRNA | miRBase Accession number |
|---|---|
| miRNA-378 | MI0000786 |
| miRNA-145 | MI0000461 |
| miRNA-150 | MI0000479 |
| miRNA-185 | MI0000482 |
| miRNA-21 | MI0000077 |
| miRNA-484 | MI0002468 |
| miRNA-625 | MI0003639 |
| miRNA-122 | MI0000442 |
| miRNA-320 | MI0000542 |
| miRNA-335 | MI0000816 |
| miRNA-365 | MI0000767 |
| miRNA-342-3p | MIMAT0000753 |

The term "responder" refers to a pancreatic cancer subject that will respond to gene therapy and gemcitabine combination treatment. The disease activity can be measured according to the standards recognized in the art. The disease activity may be measured by clinical and physical examination, Karnofsky-score evaluation, a complete blood count, hemostasis, biochemical analyses (including hepatic enzymes, lipase, and creatinine), urine analysis, disease assessment by computed tomography (CT) and progression-free survival or overall survival. A "responder" or "responsive" subject to a gene therapy and gemcitabine combination treatment refers to a subject who shows or will show a clinically significant relief in the disease when treated with a gene therapy and gemcitabine combination treatment.

The term "blood sample" refers to blood sample, a whole blood sample, a plasma sample, or a serum sample.

A further aspect of the invention relates to a method of determining whether a subject afflicted with pancreatic cancer will be a responder or a non-responder to a gene therapy and gemcitabine combination treatment comprising the step of measuring the expression level of alpha-2-macroglobulin in a blood sample obtained from said subject before the treatment.

A further aspect of the invention relates to a method of determining whether a subject afflicted with pancreatic cancer will be a responder or a non-responder to a gene therapy and gemcitabine combination treatment comprising the step of measuring the expression level of A2MG and at least one biomarker selected from K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p in a blood sample obtained from said subject before the treatment.

In a particular embodiment, the expression levels of A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p are measured.

The method of the invention may further comprise a step consisting of comparing the expression level of at least one biomarker selected from A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p in the blood sample with a reference value, wherein detecting differential in the expression level of the biomarker between the blood sample and the reference value is indicative that said subject will be a responder or a non-responder.

A reference value is determined for each biomarker. Typically, the reference value can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the biomarkers expression levels (obtained according to the method of the invention with a defined threshold value). In one embodiment of the present invention, the threshold value is derived from the biomarkers expression level (or ratio, or score) determined in a blood sample derived from one or more subjects who are responders to gene therapy and gemcitabine combination treatment. In one embodiment of the present invention, the threshold value may also be derived from biomarker expression level (or ratio, or score) determined in a blood sample derived from one or more subjects who are non-responders to gene therapy and gemcitabine combination treatment. Furthermore, retrospective measurement of the biomarker expression levels (or ratio, or scores) in properly banked historical subject samples may be used in establishing these threshold values.

In a particular embodiment, the reference value may be determined by carrying out a method comprising the steps of a) providing a collection of blood samples obtained from subjects before the gene therapy and gemcitabine combination treatment b) providing, for each blood sample provided at step a), information relating to the actual clinical outcome (response or no response);

c) providing a serial of arbitrary quantification values;

d) determining the level of the biomarker for each blood sample contained in the collection provided at step a);

e) classifying said blood samples in two groups for one specific arbitrary quantification value provided at step c), respectively: (i) a first group comprising blood samples that exhibit a quantification value for level that is lower than the said arbitrary quantification value contained in the said serial of quantification values; (ii) a second group comprising blood samples that exhibit a quantification value for said level that is higher than the said arbitrary quantification value contained in the said serial of quantification values; whereby two groups of blood samples are obtained for the said specific quantification value, wherein the blood samples of each group are separately enumerated;

f) calculating the statistical significance between (i) the quantification value obtained at step e) and (ii) the actual clinical outcome of the subjects (i.e. response or not response) from which blood samples contained in the first and second groups defined at step f) derive;

g) reiterating steps f) and g) until every arbitrary quantification value provided at step d) is tested;

h) setting the said reference value as consisting of the arbitrary quantification value for which the highest statistical significance (most significant) has been calculated at step g).

For example the level of the biomarker has been assessed for 100 blood samples of 100 subjects. The 100 samples are ranked according to the level of the biomarker. Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding subjects, the p value between both subsets was calculated. The reference value is then selected such as the discrimination based on the criterion of the minimum p value is the strongest. In other terms, the level of the biomarker corresponding to the boundary between both subsets for which the p value is minimum is considered as the reference value. It should be noted that the reference value is not necessarily the median value of levels of the biomarker.

The setting of a single "cut-off" value thus allows discrimination between responder or non responder. Practically, high statistical significance values (e.g. low P values) are generally obtained for a range of successive arbitrary quantification values, and not only for a single arbitrary quantification value. Thus, in one alternative embodiment of the invention, instead of using a definite reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, on a hypothetical scale of 1 to 10, if the ideal cut-off value (the value with the highest statistical significance) is 5, a suitable (exemplary) range may be from 4-6. Therefore, a subject may be assessed by comparing values obtained by measuring the level of the biomarker, where values greater than 5 reveal that the subject will be a responder (or alternatively a non responder) and values less than 5 reveal that the subject will be a non responder (or alternatively a responder). In another embodiment, a subject may be assessed by comparing values obtained by measuring the level of the biomarker and comparing the values on a scale, where values above the range of 4-6 indicate that the subject will be a responder (or alternatively a non responder) and values below the range of 4-6 indicate that the subject will be a non responder (or alternatively a non responder), with values falling within the range of 4-6 indicating an intermediate response.

In one embodiment, higher expression level of at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p and lower expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB are indicative that the subject will be a responder to gene therapy and gemcitabine combination treatment, and accordingly lower expression level of at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p and higher expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB are indicative that the subject will be a non-responder to gene therapy and gemcitabine combination treatment.

In one embodiment, the reference value may correspond to the expression level determined in a blood sample derived from one or more subjects who are responders to gene therapy and gemcitabine combination treatment. Accordingly, when the expression level determined for at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p is equal or higher than the corresponding reference value and/or the expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB is equal or lower than the corresponding reference value, it is concluded that the subject will be a responder to gene therapy and gemcitabine combination treatment, and accordingly, when the expression level determined for at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p is lower than the corresponding reference value and/or the expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB is higher than the corresponding reference value, its concluded that the subject will be a non-responder to gene therapy and gemcitabine combination treatment.

In another embodiment, the reference value may correspond to the expression level determined in a blood sample derived from one or more subjects who are non-responders to gene therapy and gemcitabine combination treatment. Accordingly, when the expression level determined for at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p is higher than the corresponding reference value and/or the expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB is lower than the corresponding reference value, it is concluded that the subject will be a responder to gene therapy and gemcitabine combination treatment, and accordingly, when the expression level determined for at least one biomarker selected from the group consisting of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p is equal or lower than the corresponding reference value and/or the expression level of at least one biomarker selected from the group consisting of IGHG4, FIBG, AACT, HRG, KING1, FETUA, PLMN, THRB, KLBK1, APOH, FHR5, M3K19, CLUS, PROS, C4BP4 and FIBB is equal or higher than the corresponding reference value, its concluded that the subject will be a non-responder to gene therapy and gemcitabine combination treatment.

In another particular embodiment, a score which is a composite of the expression levels of the different biomarkers may also be determined and compared to a reference value wherein a difference between said score and said reference value is indicative whether said subject is a responder or a non-responder to gene therapy and gemcitabine combination treatment.

In a particular embodiment, the score may be generated by a computer program.

Analyzing the biomarkers expression level may be assessed by any of a wide variety of well-known methods for detecting expression of a transcribed nucleic acid or translated protein.

In a preferred embodiment, the biomarkers expression level is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the protein translated from the gene encoding for the biomarkers.

Said analysis can be assessed by a variety of techniques well known from one of skill in the art including, but not limited to, enzyme immunoassay (EIA), radioimmunoassay (RIA), Western blot analysis and enzyme linked immunoabsorbant assay (RIA).

In another embodiment, the biomarkers expression level is assessed by analyzing the expression of mRNA transcript or mRNA precursors, such as nascent RNA, of biomarkers gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFFYMETRIX).

Advantageously, the analysis of the expression level of mRNA transcribed from the gene encoding for biomarkers involves the process of nucleic acid amplification, e. g., by RT-PCR (the experimental embodiment set forth in U.S. Pat. No. 4,683,202), ligase chain reaction (Barany, 1991), self sustained sequence replication (Guatelli et al., 1990), transcriptional amplification system (Kwoh et al., 1989), Q-Beta Replicase (Lizardi et al., 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

According to the invention, measuring the expression level of the miRNA selected from the group consisting of miR-378, miR-145, miR-150, miR-185, miR-21, miR-484, miR-625, miR-122, miR-320, miR-335, miR-365 and miR-342-3p of the invention in the blood sample obtained from the subject can be performed by a variety of techniques.

For example the nucleic acid contained in the samples (blood prepared from the subject) is first extracted according to standard methods, for example using lytic enzymes or chemical solutions or extracted by nucleic-acid-binding resins following the manufacturer's instructions. Conventional methods and reagents for isolating RNA from a blood sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), miRNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

The expression level of one or more miRNA in the blood sample may be determined by any suitable method. Any reliable method for measuring the level or amount of miRNA in a sample may be used. Generally, miRNA can be detected and quantified from a blood sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In some embodiments, the expression level of miRNA is measured during the amplification process. In some embodiments, the expression level of miRNA is not amplified prior to measurement. Some exemplary methods suitable for determining the expression level of miRNA in a sample are described in greater hereinafter. These methods are provided by way of illustration only, and it will be apparent to a skilled person that other suitable methods may likewise be used.

Many amplification-based methods exist for detecting the expression level of miRNA nucleic acid sequences, including, but not limited to, PCR, RT-PCR, qPCR, and rolling circle amplification. Other amplification-based techniques include, for example, ligase chain reaction (LCR), multiplex ligatable probe amplification, in vitro transcription (IVT), strand displacement amplification (SDA), transcription-mediated amplification (TMA), nucleic acid sequence based amplification (NASBA), RNA (Eberwine) amplification, and other methods that are known to persons skilled in the art. A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence. In some embodiments, custom qRT-PCR assays can be developed for determination of miRNA levels. Custom qRT-PCR assays to measure miRNAs in a sample can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in the samples. Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2(−ΔΔ C(T)) Method, as described by Livak et ah, Analysis of relative gene expression data using real-time quantitative PCR and the 2(−ΔΔ C(T)) Method. Methods (2001) December; 25(4):402-8.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al, Am. J. Pathol. (2001) 159(0:63-69; Nallur et al, Nucleic Acids Res. (2001) 29(23):E118). In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al, Chembiochem. (2009) 10(8): 1289-91).

miRNAs quantification method may be performed by using stem-loop primers for reverse transcription (RT) followed by a real-time TaqMan® probe. Typically, said method comprises a first step wherein the stem-loop primers are annealed to miRNA targets and extended in the presence of reverse transcriptase. Then miRNA-specific forward primer, TaqMan® probe, and reverse primer are used for PCR reactions. Quantitation of miRNAs is estimated based on measured CT values.

Many miRNA quantification assays are commercially available from Qiagen (S. A. Courtaboeuf, France), Exiqon (Vedbaek, Denmark) or Applied Biosystems (Foster City, USA).

Expression level of miRNAs may be expressed as absolute expression level or normalized expression level. Typically, expression levels are normalized by correcting the absolute expression level of miRNAs by comparing its expression to the expression of a mRNA that is not a relevant for determining subject who will be a responder or a non-responder to a gene therapy and gemcitabine combination treatment, e.g., a housekeeping mRNA that is constitutively expressed. Suitable mRNA for normalization include housekeeping mRNAs such as the U6, U24, U48 and S18. This normalization allows the comparison of the expression level in one sample, e.g., a subject sample, to another sample, or between samples from different sources. In a particular embodiment, expression levels are normalized by correcting the absolute expression level of miRNAs by comparing its expression to the expression of a reference miRNA such as miR-92a.

Nucleic acids exhibiting sequence complementarity or homology to the miRNAs of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

The probes and primers are "specific" to the miRNAs they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, inkjet printing, or electrochemistry on microelectrode arrays. Also useful are microfluidic TaqMan Low-Density Arrays, which are based on an array of microfluidic qRT-PCR reactions, as well as related microfluidic qRT-PCR based methods. In one example of microarray detection, various oligonucleotides (e.g., 200+ 5'-amino-modified-C6 oligos) corresponding to human sense miRNA sequences are spotted on three-dimensional CodeLink slides (GE Health/Amersham Biosciences) at a final concentration of about 20 µM and processed according to manufacturer's recommendations. First strand cDNA synthesized from 20 µg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol. Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs. For example, RNA can be extracted from the sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. Total RNA containing the miRNA extracted from the sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA. Several types of microarrays can be employed including, but not limited to, spotted oligonucleotide microarrays, pre-fabricated oligonucleotide microarrays or spotted long oligonucleotide arrays.

Accordingly, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook-A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antl1ranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfor1ic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4, 6dicl1lorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716, 979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (Quantum-Dot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., Science 281:20132016, 1998; Chan et al., Science 281: 2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlsbad, Calif.).

RT-PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. The majority of the thermocyclers on the market now offer similar characteristics. Typically, thermocyclers involve a format of glass capillaries, plastics tubes, 96-well plates or 384-wells plates. The thermocylcer also involve a software analysis.

miRNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar miRNAs with great specificity. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the tumor sample with a probe library, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Mass spectroscopy can be used to quantify miRNA using RNase mapping. Isolated RNAs can be enzymatically digested with RNA endonucleases (RNases) having high specificity (e.g., RNase T1, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of posttranscriptional modifications can be revealed by mass shifts from those expected based upon the RNA sequence. Ions of anomalous mass/charge values can then be isolated for tandem MS sequencing to locate the sequence placement of the posttranscriptionally modified nucleoside. Matrix-assisted laser desorption/ionization mass spectrometry (MALDI-MS) has also been used as an analytical approach for obtaining information about posttranscriptionally modified nucleosides. MALDI-based approaches can be differentiated from ESTbased approaches by the separation step. In MALDI-MS, the mass spectrometer is used to separate the miRNA. To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels. miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.). Northern Blot and in situ hybridization may also be used to detect miRNAs. Suitable methods for performing Northern Blot and in situ hybridization are known in the art. Advanced sequencing methods can likewise be used as available. For example, miRNAs can be detected using Illumina® Next Generation Sequencing (e.g. Sequencing-By-Synthesis or TruSeq methods, using, for example, the HiSeq, HiScan, GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semiconductor sequencing.

In a further aspect, the present invention relates to a method of determining whether a subject afflicted with pancreatic cancer will be a responder or a non-responder to a gene therapy and gemcitabine combination treatment comprising the steps of:

(i) measuring the expression level of at least one biomarker selected from A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p in a blood sample obtained from said subject before the treatment, (ii) comparing the expression level measured at step i) with a reference value, (iii) detecting differential in the biomarker expression level between the blood sample and the reference value is indicative that said subject will be a responder or a non-responder.

The invention also relates to a kit for performing the methods as above described, wherein said kit comprises means for measuring the expression level of at least one biomarker selected from A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p that is indicative of subject responder to gene therapy and gemcitabine combination treatment. Typically the kit may include primers, probes, an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards.

Methods of Treatment

The method of the invention allows to define a subgroup of subjects who will be responder or non responder to the gene therapy and gemcitabine combination treatment.

A further aspect of the invention relates to a method for treating pancreatic cancer in a subject in need thereof comprising the steps of:

a) determining whether a subject afflicted with pancreatic cancer will be a responder or a non-responder to a gene therapy and gemcitabine combination treatment by performing the method according to the invention, b) administering the gene therapy and gemcitabine combination treatment, if said patient has been considered as a responder.

A further aspect of the invention relates to a gene therapy and gemcitabine combination for use in the treatment of pancreatic cancer in a subject in need thereof, wherein the subject was being classified as responder by the method as above described.

A further aspect of the invention relates to a method for chemosensitization of advanced pancreatic cancer in a subject in need thereof comprising the steps of:

a) determining whether a subject afflicted with advanced pancreatic cancer will be a responder or a non-responder to a gene therapy and gemcitabine combination treatment by performing the method according to the invention, b) administering the gene therapy and gemcitabine combination treatment, if said patient has been considered as a responder.

A further aspect of the invention relates to a gene therapy and gemcitabine combination for use in the treatment of advanced pancreatic cancer in a subject in need thereof, wherein the subject was being classified as responder by the method as above described.

The invention will be further illustrated by the following figures and examples. However, these examples and figures should not be interpreted in any way as limiting the scope of the present invention.

FIGURES

FIG. 1: Clinical trial flowchart and injection of the gene therapy product in patients.

(a) Flowchart of the THERGAP trial for advanced pancreatic cancer. Patients received two intratumoral injections of CYL-02 using endoscopic ultrasound (EUS) followed by gemcitabine infusions. Complete clinical examinations and biological assessments were performed during each visit and twice on the day of the CYL-02 injections (days 1 and 28, at 1 h before and 6 h after CYL-02 injections). Blood samples were obtained from patients during each visit (twice on the day of the CYL-02 injection: before and 6 h after) and were processed for serum and plasma (EDTA-treated tubes) preparations. Urine was collected before and at 24 and 48 h after CYL-02 injection. The tumour marker CA 19-9 was quantified before (visit 0 and day 1) and at 2 months (day 60) following treatment. V: Visit. For intratumoral gene transfer, lyophilized CYL-02 was reconstituted by adding 2.5 mL of sterile water 10 min before starting EUS. Gene therapy was performed under general anesthesia. (b): pancreatic carcinoma of the body. The tumour is delineated with a white dashed line. The biopsy needle was then positioned at the center of the tumour (c): needle (with arrows) using EUS guidance within the tumour (dashed arrow indicates the hyper-echoic needle tip) and, after removing the stylet, CYL-02 was slowly injected using backwards and forwards movements, including a fanning technique of the needle within the tumour under ultrasound control (d): Pancreatic carcinoma of the body immediately following CYL-02 injection showing a white cloud within the tumour (delineated by the arrows). At the end of the procedure, 1.5 mL of 5% glucose (w/v) solution was injected within the tumour to empty the needle.

FIG. 2: Biodistribution and expression of the gene therapy product.

(a) CYL-02 was detected by qPCR at the time indicated in the blood of patients receiving 1000 μg of the gene therapy product. * indicates 6 hours post intratumoral injection of CYL-02. Data are means±SD of 4 biological replicates per group with 3 experimental replicates and expressed as copies per mL of blood. Experimental threshold: 10 copies/ml of blood; experimental background in blood: $7.8 \pm 0.2 \times 10^4$ copies per mL of blood. (b) CYL-02 DNA was detected by qPCR in the tumours of patients at one month following gene therapy. Data are means±SD of 4 (patients receiving 250 and 1000 μg of CYL-02) or 6 (patients receiving 500 μg of CYL-02) biological replicates per group with 3 experimental replicates and expressed as copy numbers of CYL-02 per ng of tumor DNA. For statistical comparison of two experimental groups, the bilateral Student's t-test was used (*: p<0.05). Experimental threshold: 10 copies/ng of DNA; experimental background in tumours: 0 copies/ng of DNA. (c) DCK::UMK and SSTR2 genes expression were measured in tumours before and one month following gene therapy with 1000 μg of CYL-02. Data are means±SD of 4 (patients receiving 1000 μg of CYL-02) biological replicates per group with 3 experimental replicates and expressed as arbitrary units ($2^{-\Delta Ct}$ with $\Delta Ct = CT$ (DCK::UMK or SSTR2)−CT(18S)). For statistical comparison of two experimental groups, the non-parametric Wilcoxon test was used (***: p<0.005).

Figure 3:
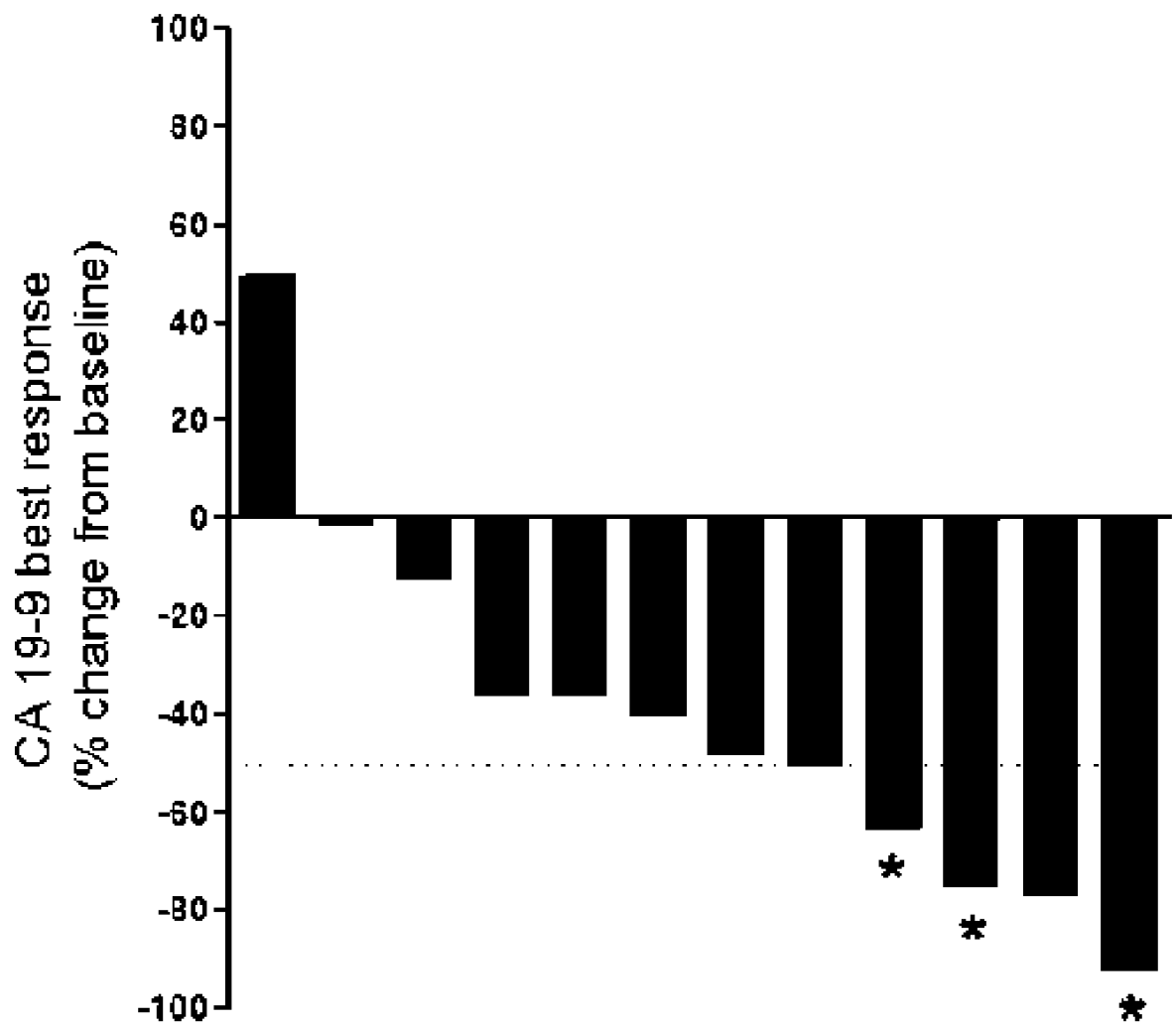

FIG. 3: Radiological findings and clinical efficacy of gene therapy.

CA 19.9 was measured in the blood of 13 patients with locally advanced pancreatic cancer before and at the completion of the gene therapy protocol. Data are expressed as % change from baseline. Dotted line indicates 50% inhibition threshold. * indicates prior treatment.

Figure 4A:
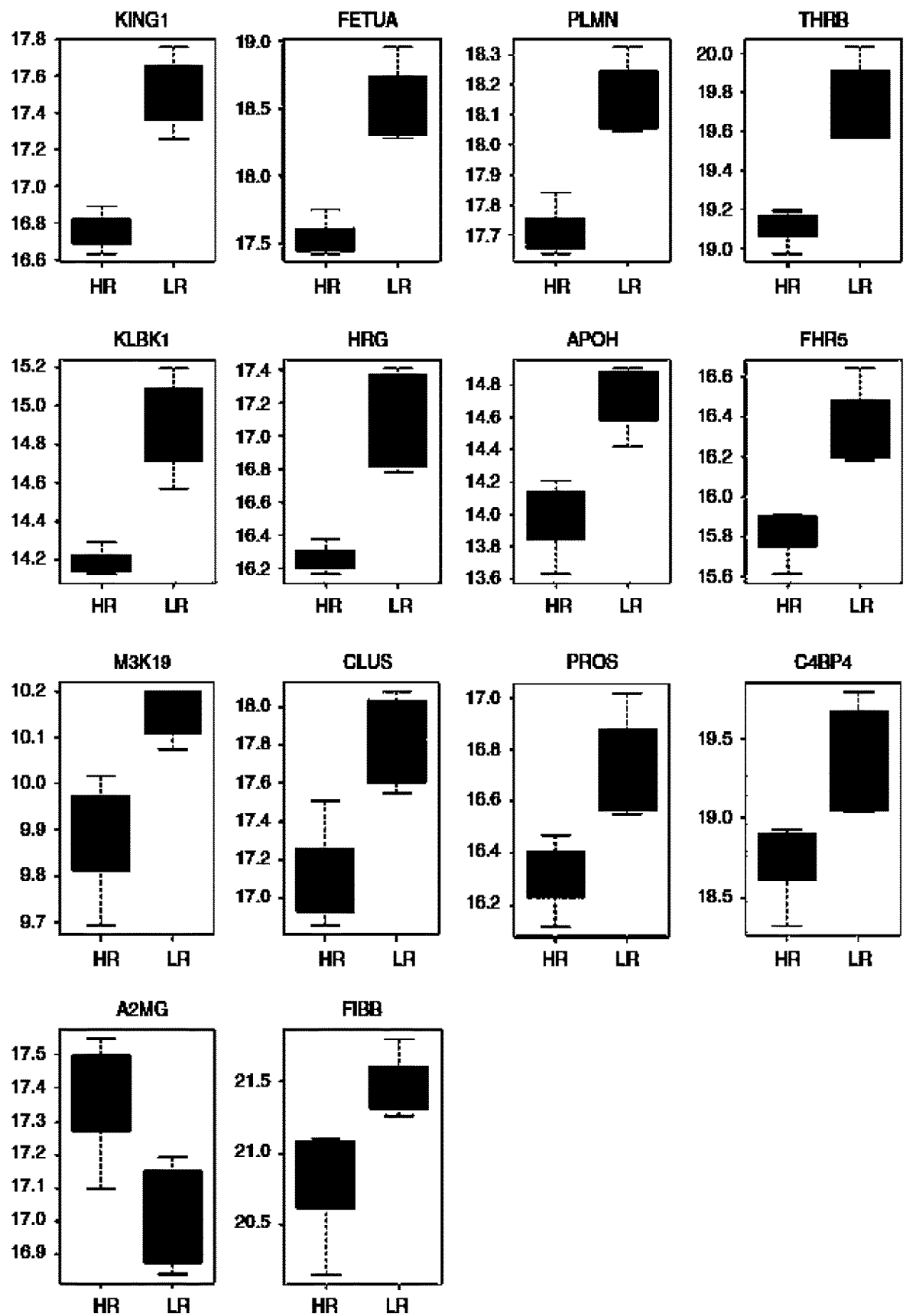

FIG. 4: Biomarker discovery.

(A) Individual Box plots for the circulating proteins predictive of efficacy identified in this study. Results are expressed as protein frequency in high-responder (HR) vs low-responder (LR) patients. (B) Quantification by ELISA of A2MG levels in patient plasma prior gene therapy. Data are expressed as protein level in ng/ml. The bilateral Student's t-test was used (*: p<0.05). (C) Individual Box plots for the circulating miRNAs predictive of efficacy identified in this study. Results are expressed as Ct in high-responder (HR) vs low-responder (LR) patients.

EXAMPLE

Material & Methods

Patient Selection

The inventors included patients aged >18 years, who had given their written informed consent, and had histologically or cytologically confirmed PDAC or a solid non-resectable pancreatic mass associated with one or multiple metastases that had been histologically proven as adenocarcinoma. Other criteria for inclusion were no contraindications for general anesthesia, a Karnofsky score of ≥70%, and a primary pancreatic tumor accessible by endoscopic ultrasound. The main exclusion criteria were known intolerance to gemcitabine, pregnancy, a non-measurable primary tumor, a tumor eligible for possible neo-adjuvant treatment by radio-chemotherapy, or a contraindication for EUS-guided fine needle aspiration (FNA).

Treatment Plan

CYL-02 is a complex of plasmid DNA and linear polymers of polyethyleneimine (JetPEI 22-kDa from Polyplus), prepared in 5% w/v glucose with a PEI nitrogen to DNA phosphate (N/P) ratio of 8 to 10. The plasmid within the gene therapy product encodes for DCK::UMK cDNAs (separated by the self-cleaving FMDV 2A peptide), and the human SSTR2 cDNA. Both DCK::UMK and SSTR2 cDNAs are under the coordinated transcriptional control of Glucose Responsive promoters (GRP78 and GRP94, respectively) that are highly sensitive to stress conditions[29], which prevails inside pancreatic tumors[30]. The prokaryotic promoter-driven neomycin gene is used for bacterial selection and biodistribution and pharmacokinetic studies. The gene-therapy product is assembled and lyophilized by InvivoGen (Toulouse, France), following good medical product guidelines.

The THERGAP (gene therapy for advanced pancreatic adenocarcinoma) protocol was approved by the Ethical Committee (Comité de Protection des Personnes Sud-Ouest et Outre Mer N° 1, number 1-10-21) on August 2010 (promoter CHU of Toulouse), and by the AFSSAPS (N° TG.10.05.01) and the HCB (N° 4883) on November 2010 (EUDRACT number: 2006-005317-35-A; Clinical Trial NCT01274455). After signed informed consent, the patients were enrolled (BB, LB, RG) for a 2-month period to receive two intratumoral injections of CYL-02 followed by gemcitabine infusions (1000 mg/m$^2$) starting 48 h after injection of the gene-therapy product and following every week for 3 weeks. The inventors extrapolated the active dose of CYL-02 characterized in hamsters to human equivalent dose (250 µg of complexed DNA per patient) using body surface area normalization method corrected by the animal clearance according to the European Medicines Agency recommendation M3-R2.

Drug Administration

Lyophilized CYL-02 was reconstituted in individual CYL-02 flasks by adding 2.5 mL of sterile water 10 min before starting EUS. This was performed (LB, BB) under general anesthesia with propofol, using an Olympus GFUCT-140 echoendoscope connected to an Aloka Alpha5 ultrasound probe. Examination was started by visualization (with a 5-10-MHz ultrasound probe that included power-Doppler analysis) and measurement of the primary tumor and possible lymph nodes or metastases (peritoneum, liver). The biopsy needle (22-G EUS-N1 needle, Wilson-Cook) was then positioned at the center of the tumor and, after removing the stylet, CYL-02 was slowly injected using backwards and forwards movements, including a fanning technique of the needle within the tumor under ultrasound control. At the end of the procedure, 1.5 mL of 5% glucose (w/v) solution was injected within the tumor to empty the needle. After removing the needle, an examination of the tumor and its surrounding was performed (including Doppler analysis), to assess the spread of the gene-therapy product and the absence of local complications. Monitoring (assessment of blood pressure, pulse, oxygen saturation, ventilation frequency each minute) was performed during and for 30 min after the CYL-02 injection. EUS examinations were recorded on CD-ROMs for subsequent reviews. Gemcitabine was delivered intravenously at a dose of 1000 mg/m$^2$ of body-surface area for 30-min at 48 h after the CYL-02 injections. Gemcitabine injections were repeated weekly for 3 weeks at the same dose.

Assessments, Follow-Up and Monitoring

The Center for Clinical Investigation of Biotherapies of Toulouse (CIC-BT 511) and the promoter (CHU of Toulouse) monitored the clinical trial. Following consent, patients underwent a clinical and physical examination, Karnofsky-score evaluation, a complete blood count, hemostasis, biochemical analyses (including hepatic enzymes, lipase, and creatinine), urine analysis, a pregnancy test, and disease assessment by computed tomography (CT) on visit 0 and EUS examination on day 1. Complete clinical examinations and biological assessments were performed during each visit and twice on the day of the CYL-02 injections (days 1 and 28, at 1 h before and 6 h after CYL-02 injections). The tumor marker CA 19-9 was assessed before (day 1) and at 2 months (day 60) following treatment. Adverse events were graded according to the National Cancer Institute Common Terminology Criteria of Adverse Events (version 3). Patients were only considered evaluable for the phase-1 study if two injections of CYL-02 had been performed plus at least two of the three gemcitabine infusions. RECIST criteria (version 1.1) were used to measure disease response at 2 months. At the end of the protocol, the symptoms, disease progression, Karnofsky and OMS statuses, and co-morbidities were analyzed, and a multidisciplinary decision was made on the follow-up treatment according to the French National Guidelines for Digestive Cancers. In case of stable disease, gemcitabine was maintained for 4 weeks (i.e., weekly for 3 weeks followed by one week off), for four months. For progressive disease (either after the 2-month protocol or during the subsequent gemcitabine treatment), another protocol of chemotherapy or best supportive care was implemented. All patients were followed-up monthly and CT evaluation was performed every 2 months. The inventors recorded any new clinical events, CA 19-9 levels, and progression of the disease after CT, and the date and cause of death.

Treatment Following Gene Therapy+Gemcitabine Cycles

Following gene therapy+gemcitabine cycles, Patients #4, 8, 11, and 15 received best supportive care. Patient #3 received Xeloda then best supportive care. Patient #5 received Anti kin then best supportive care. Patient #16 received Folfox, then Xeloda, then best supportive care. As mentioned before, patients with locally advanced tumors and stable disease following gene therapy and chemotherapy cycles were further treated for 4 months with gemcitabine only (Patients #2, 6, 9, 10, 12, 13, 14, 17; 19, 20, 21 and 22). As a third line (i.e. second line following gene therapy+chemotherapy), patients received Folfox (Patients #12 and 13), radiochemotherapy (Patient #14 and 20) or best supportive care (Patients #2, 6, 9, 17, 21 and 22). Patients #12 and 20 received best supportive care as fourth line, while Patients #14 and 19 received Folfox or LV5-FU2, respectively, then best supportive care. All Patients died from cancer.

Definition of MTD and Dose Escalation Plan

The maximal tolerated dose (MTD) was defined as the highest dose level of CYL-02 at which 1 or less of 6 patients experienced severe acute pancreatitis or died from the experimental treatment, or had major diffusion of CYL-02 into the blood and/or urine during cycle 1. The trial used the standard 6+6 dose escalation design. The study drug dose was escalated to the next higher level if none of the 6 patients developed MTD criteria, as defined above. Dose-escalation ranged from 125 to 1000 µg of complexed DNA (six patients received 125, 250, or 500 µg, and four patients received 1000 µg). Dose escalations were under the supervision of an independent committee of experts. Nonevaluable patients were not replaced.

Pharmacokinetic Sampling and Analytic Assay

Blood samples were obtained from patients during each visit (twice on the day of the CYL-02 injection: before and 6 h after). Venous blood samples were collected, and processed for serum and plasma (EDTA-treated tubes). Samples were stored at −80° C. Urine was also collected before and at 24 and 48 h after CYL-02 injection. CYL-02 DNA levels were quantified by qPCR. Briefly, total DNA was isolated from whole-blood and urine using a QIAamp DNA Mini Kit (Qiagen). Nucleic acids were quantified using ND-1000 NanoDrop spectrophotometry. Triplicate qRT-PCR assays were carried out on 50 ng of DNA extracted from urine or blood from patients in a SYBR Green PCR Master Mix (SsoFast, Biorad,) with primers directed against the neomycin gene (NeoF and NeoR), using a StepOne II (Life Technologies). CYL-02 levels were expressed as copy numbers/ml of blood.

Tumor Analysis

Fine needle aspiration biopsies were obtained from tumors before (V0) and one month following gene therapy (V7) using a 22-G EUS-N1 needle (Wilson Cook). Fine-needle aspiration biopsies were performed before the second injection of CYL-02. The tissue/cellular materials were divided into two and placed within formalin or RNABle (Qiagen) before performing a histological examination and nucleic-acid extraction, respectively. DNA and total RNA were extracted from formalin-fixed, paraffin-embedded tissues from baseline biopsies using RecoverAll™ Total Nucleic Acid Isolation Kit (Life technologies, Saint Aubin, France) following the manufacturers' recommendations. AllPrep DNA/RNA/miRNA Universal Kit (Qiagen) was used to process fine-needle aspirates (FNA) material dropped in RNALater from patients 1 month after gene therapy. CYL-02 DNA was quantified as described above. For gene expression studies, aliquots of 50 ng of total RNA were used for reverse transcription using a RevertAid First Strand cDNA Synthesis Kit (Thermo Scientific, Marnes-la-Coquette, France) before Specific Target Amplification (STA) to increase target concentration. Triplicate qRT-PCR assays were carried out in a ViiA7™ Real-Time PCR System (Life Technologies), in a SYBR Green PCR Master Mix (SsoFast, Biorad) using: pN1R5 and pN1F5-7 primers to quantify DCK::UMK gene expression, and D6573B04 and D6573B05 primers to quantify SSTR2 expression, respectively. 18S RNA expression was used as calibrator, as previously described (18). Relative amounts were calculated by the comparative cycle threshold (CT) method as 2-ΔCT, where ΔCT=CT(DCK::UMK or SSTR2)–CT(18S). Samples with CT(18S)<28 were considered for analysis.

Biomarker Discovery

Circulating miRNAs. Total RNAs were extracted from patients' plasma using Trizol LS (Life technologies) following the manufacturers' recommendations. Plasmatic microRNAs were quantified in 200 ng of total RNA using QuantStudio™ 12K Flex OpenArray® microRNA plates and Megaplex™ Primer Pools according to the manufacturer's instructions. Each TaqMan® OpenArray® Human MicroRNA Panel, QuantStudio™ 12K Flex contains 754 well-characterized human microRNA sequences from the Sanger miRBase v14.

Proteomic studies. ProteoMiner protein enrichment kit was used according to Bio-Rad's instructions on 50 µl of plasma. Proteins were eluted from beads, reduced, alkylated before running on SDS-PAGE. Proteins were stained by Coomassie Blue, each lane was cut and each gel piece was washed several times in acetonitrile 100%, ammonium bicarbonate 100 mM and dried in vacuo. Gel pieces were rehydrated with 20 ng/µl trypsin prepared in 100 mM ammonium bicarbonate, and digested overnight at 37° C. Peptides were then extracted and subjected to mass spectrometry analysis. The peptides mixtures were analysed by nanoHPLC-chip-MS/MS with a system consisting of a nano-pump, a capillary-pump (G1376A and G2226, Agilent) with two four-channel micro-vacuum degasser (G1379B, Agilent), a microfluidic chip cube (G4240-64000, Agilent) interfaced to an Amazon ETD mass spectrometer (Bruker Daltonics). A microfluidic reversed-phase HPLC chip (Zorbax 300SB-C18, 5 µm particle size, 75 µm internal diameter, and 150 mm length) was used for peptide separation. Peptides were eluted and scans MS were acquired on the 300-1500 m/z range in the enhanced resolution mode. For peptide fragmentation, the Amazon was operated in data dependent acquisition mode with the trap control software. Scans The Bruker data files (.d folder) generated with the Chip-MS technology were loaded to Progenesis LC-MS version 4.0 (Nonlinear Dynamics). Peak picking was performed to detect features (i.e. ions detected on the mass spectrometer) using automatic parameters for sensitivity and retention time window. Statistical filters were set and only features matching all filters were kept. Filters used was p-value<5% (Student's t-test) A csv file was then exported from Progenesis and loaded to R 2.13.2. Descriptive statistics and Principal Component Analysis (PCA) were performed using mixOmics R Package.22. As potential biomarkers, relevant features selected by Progenesis were exported in .mgf files and the corresponding proteins were identified using the MASCOT software (http: //www.matrixscience.com) and SwissProt database (http://web.expasy.org/docs/swiss-prot_guideline.html). Mascot files were then imported in Progenesis software to select the most relevant identified proteins.

Statistical Analysis

All data are presented as mean±SD. For statistical comparison of two experimental groups, the non-parametric Wilcoxon test was used (* $p<0.05$,  $p<0.01$; * $p<0.005$) using Graphpad Prism software (Graphpad Software). A level of $p<0.05$ was considered statistically significant. No statistical method was used to predetermine sample size. The experiments were randomized. During the gene therapy clinical trial, Patients were not selected with respect to the dose administered. The investigators were not blinded to allocation during experiments except for tumor growth experiments in preclinical models, DNA and (micro)RNA quantification and histological examinations. No animals were excluded from the preclinical study. For proteomic studies, descriptive statistics are presented as principal component analysis (PCA) that allows exploratory data analysis combining samples and proteins. A Tukey test was used to analyze coefficient of variation (CV) in order to compare variability between groups and variability within groups. Statistical analyses were done with FactoMineR package for R software (http://cran.r-project.org/web/packages/FactoMineR/).

Results

Patient Characteristics

A total of 22 patients with advanced pancreatic cancer were consented and received treatment between December 2010 and September 2012. The demographic and clinical characteristics of the enrolled patients are listed in Table 1. Thirteen patients were diagnosed with locally advanced disease, while 9 patients had distant metastasis. Four patients with locally advanced disease had received prior chemotherapy whereas 9 had not. All patients with distant metastasis excepting two had received prior chemotherapy. Among the 22 patients included, 20 patients were evaluable for safety evaluation. The gene-therapy protocol was stopped for two patients (both receiving 250 µg of CYL-02): one patient received less than two third of gemcitabine because of rapid progression of metastatic disease; the second patient had only one injection of CYL-02 because of septicaemia caused by chronic biliary-stent obstruction (these two patients had received FOLFIRINOX as a first treatment for metastatic PDAC).

TABLE 1

Demographic and baseline characteristics of the patients enrolled in the THERGAP gene therapy clinical trial
Clinical data

| | |
|---|---|
| Age (years) | Median: 61.5 |
| | Range: 50-74 |
| Gender: n (%) | Male: 15 (68%) |
| | Female: 7 (32%) |
| Pancreatic tumor localization: n (%) | Head: 11 (50%) |
| | Body: 9 (41%) |
| | Tail: 2 (9%) |
| | None: 13 (59%) |
| Metastatic cases: n (%) | Liver alone: 8 (36.5%) |
| | Liver and peritoneal: 1 (4.5%) |
| | None: 12 (54.5%) |
| First-line treatments: n (%) | Chemotherapy*: 8 (36.5%) |
| | Chemoradiotherapy: 1 (4.5%) |
| Other treatments: n (%) | Surgery**: 1 (4.5%) |
| | Biliary stent: 5 (23%) |
| | Surgical bypass: 4 (18%) |

*FOLFIRINOX and GEMOX protocols given to, respectively, six and two patients; liver metastasis occurred in the six patients that received FOLFIRINOX.
**Left pancreatectomy. Among the 22 patients included, 20 patients were evaluable.

The gene-therapy protocol was stopped for two patients (both receiving 250 μg of CYL-02): one patient received less than two-third gemcitabine infusions because of rapid progression of metastatic disease; the second patient had only one injection of CYL-02 because of septicemia caused by chronic biliary stent obstruction (these two patients had received FOLFIRINOX as a first treatment for metastatic pancreatic cancer). THERGAP, gene therapy for advanced pancreatic adenocarcinoma.

Dose-Escalation Process

Patients received two intratumoral injections of CYL-02 using endoscopic ultrasound (EUS) followed by gemcitabine infusions (FIG. 1a). Injection of escalating doses (125, 250, 500 and 1000 μg) of CYL-02 was feasible in all cases whatever the size of the primary tumor (mean maximal size measured by EUS at day 1: 36.5±2.3 mm [median 33-, range: 22-54]), the localization of the primary tumor (including uncus, isthmus, or tail in two, three, and two cases, respectively); and previous local treatment (i.e., biliary stenting, biliary or digestive bypass, partial resection). CYL-02 injections resulted in "white cloudy" shapes within the tumor easily tracked by EUS (FIG. 1b-d). No further escalation was attempted, as 1000 μg was the highest planned dose of CYL-02. The inventors declared dose level 4 (1000 μg) as the RPTD for this study.

Safety

The toxicity profile observed with the study combination was similar to that reported for gemcitabine alone. All patients received at least one dose of treatment and were evaluable for toxicity. Grade I or higher treatment-related adverse events are summarized in Table 2. There was one death at dose 500 μg (patient #18), that was not considered as related to the study treatment due to the temporal relationship, while the patient was showing indications of stable disease. Grade III-IV non-dose-limiting treatment-related toxicities included fever in two patients (9%) treated with 250 μg and 500 μg of CYL-02. The inventors conclude that the intratumoral delivery of anticancerous genes by EUS using non-viral vectors is feasible, well tolerated and safe in patients with pancreatic cancer.

TABLE 2

Adverse events related to combined treatment of CYL-02 and gemcitabine during the THERGAP gene therapy clinical trial

| Dose (patients) | 125 μg (n = 6) | 250 μg (n = 4) | 500 μg (n = 6) | 1,000 μg (n = 4) |
|---|---|---|---|---|
| Grade | 1-2/3-4 | 1-2/3-4 | 1-2/3-4 | 1-2/3-4 |
| Neutropenia | 2/0 | 1/0 | 2/0 | 1/0 |
| Anemia | 3/0 | 1/0 | 1/0 | 2/0 |
| Thrombocytopenia | 1/0 | 1/0 | 2/0 | 1/0 |
| Fever | 4/0 | 1/1 | 3/1 | 1/0 |
| Anorexia/nausea | 4/0 | 1/0 | 4/0 | 4/0 |
| Abdominal pain | 2/0 | 1/0 | 1/0 | 0/0 |
| Acute pancreatitis | 0/0 | 1/0 | 0/0 | 0/0 |
| Pruritus | 2/0 | 1/0 | 0/0 | 0/0 |
| Foot and hand syndrome | 0/0 | 0/0 | 1/0 | 0/0 |
| Hyperlipasemia | 1/0 | 0/0 | 0/0 | 1/0 |
| Increased ASAT | 0/0 | 0/0 | 4/0 | 2/0 |
| Increased ALAT | 1/0 | 0/0 | 4/0 | 2/0 |

Adverse events that may be related to the combination of CYL-02 and gemcitabine were mostly of grade 1-2, such as increase in serum alanine aminotransferase (ALAT) and aspartate aminotransferase (ASAT) levels. Two patients had significantly increased serum lipase levels (>3 N), but were free of abdominal symptoms. With the exception of a single event of transitory increase in blood pressure during CYL-02 injection, the gene therapy protocol was well tolerated by patients. Two patients experienced tumor pain immediately after gene transfer and were successfully treated by a morphine injection. Transitory fever (<12 hours) occurred at day 1 after the first injection of CYL-02 in six cases (regardless of the dose of CYL-02 administered). A case of acute pancreatitis occurred in one patient (Balthazar A-grade) and led to a 24-hour delay in gemcitabine infusion. Adverse grade 3-4 events were recorded in only two patients (fever in each case) after gemcitabine injection. THERGAP, gene therapy for advanced pancreatic adenocarcinoma.

Pharmacokinetics and Tumor Analysis

Figure 2A:
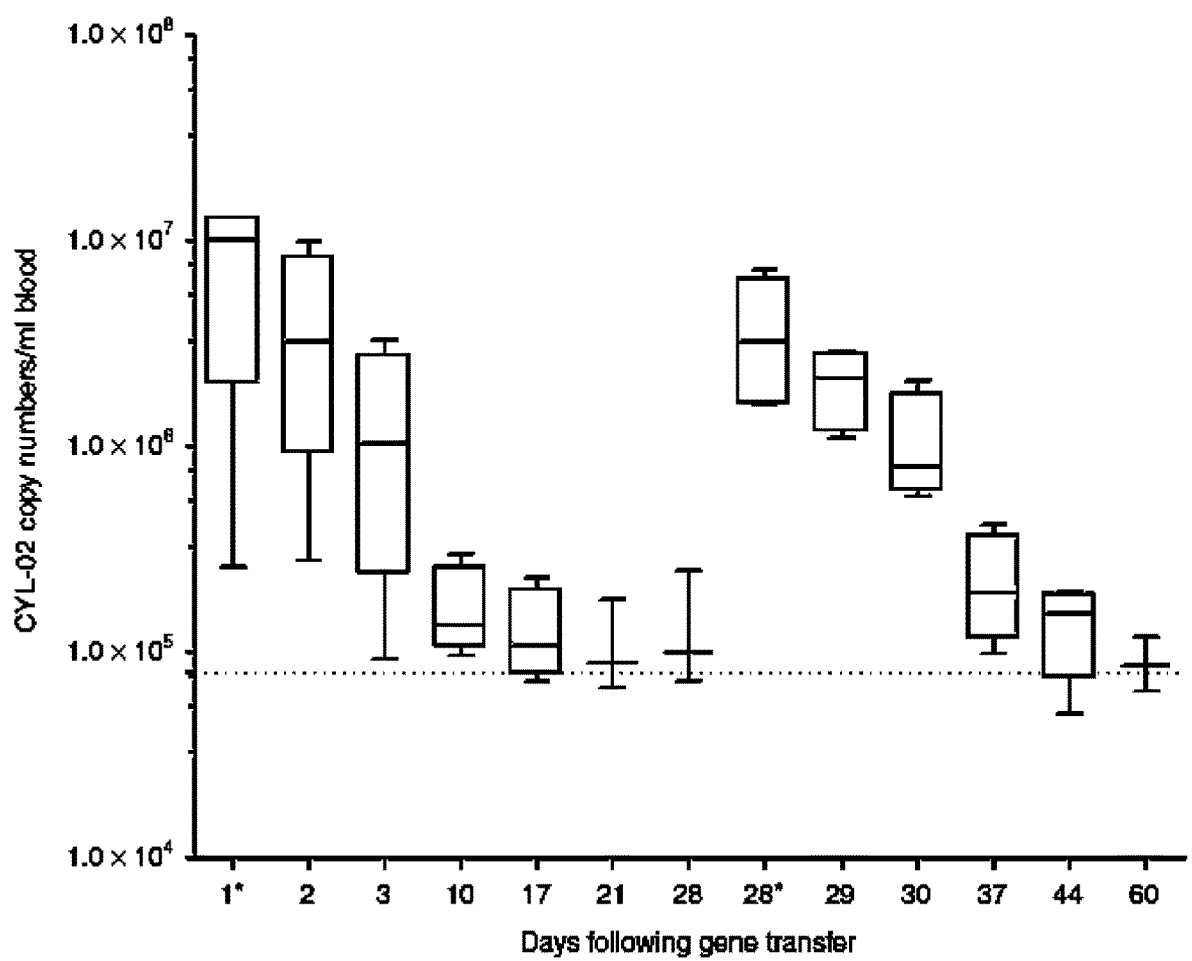
Figure 2B:
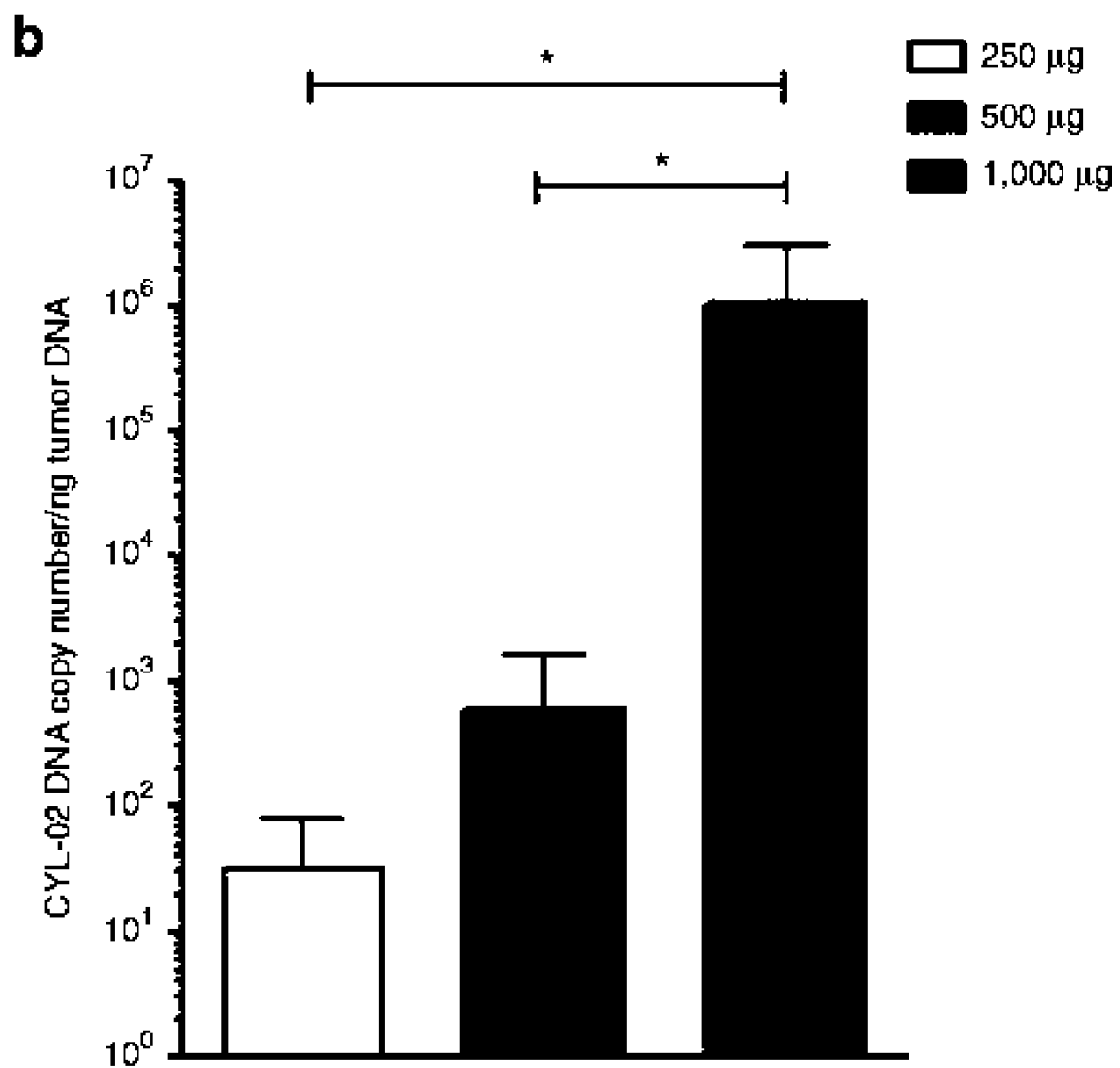

The inventors characterized the biodistribution of CYL-02 following intratumoral injection in patients. The inventors first assessed CYL-02 dissemination in urine and blood. Therapeutic DNA was not detected in the urine of treated patients with the exception of patient #13 in whom the tumor had invaded the right kidney, strongly suggesting a direct leakage of CYL-02 into the urine flow following intratumoral injection, rather than active excretion by the kidneys. On the other hand, CYL-02 DNA levels peaked in the blood of patients following each of the two-rounds of gene therapy. FIG. 2a illustrates CYL-02 dissemination at dose=1000 μg, corresponding to 0.02%±0.01% and 0.06%±0.04% of the injected dose, respectively. In addition, the amount of CYL-02 detected in the blood after the first injection tended to be proportional to the dose administrated (p=0.057, data not shown). There was no difference in the pharmacokinetic parameters of CYL-02 between day 1 and day 28.

Figure 2C:
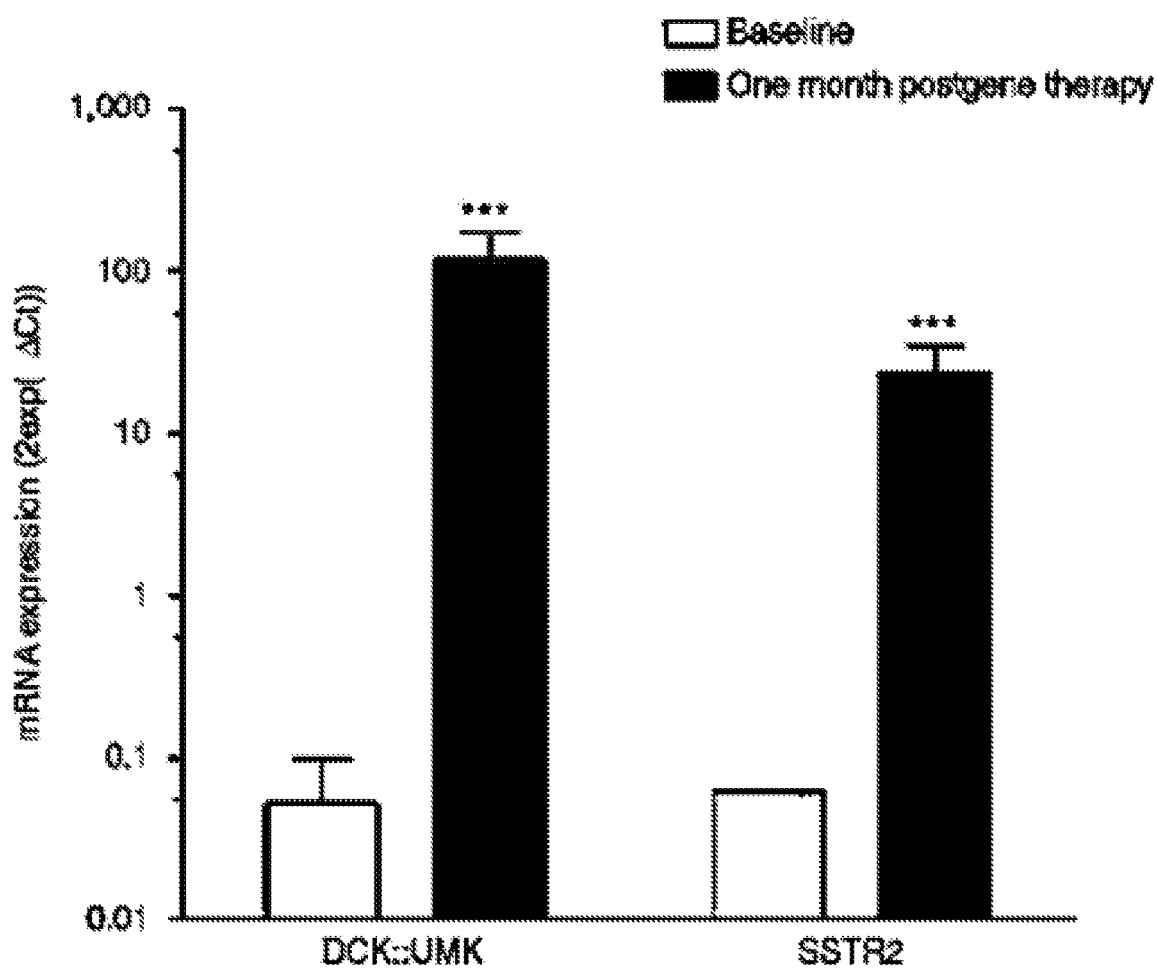

CYL-02 DNA was detected in FNA micro-biopsies collected from tumors, one month following gene transfer. Tumors from patients #2 and #3 were too small to be sampled. The inventors found that 0% (0/4), 75% (3/4, mean copy number $3.18±2.3×10^2$), 66.6% (4/6, mean copy number $5.88±4.29×10^3$), and 100% (4/4, mean copy number $1.05±1.02×10^6$) of EUS-guided tumor biopsies were positive for CYL-02 following injection with 125, 250, 500, and 1000 μg of CYL-02, respectively. CYL-02 DNA levels were statistically elevated in tumors receiving 1000 μg as compared to tumors receiving 250 or 500 μg of the gene-therapy product ($p<0.05$, FIG. 2b). Therapeutic mRNA expression was detected in 75% (3/4, mean relative expression 1.017±0.83), 100% (4/4, mean relative expression 0.89±0.87), 66.6% (5/6, mean relative expression 0.16±0.12), and 100% (4/4, mean relative expression 52.2±28.2) of patients' tumor injected with 125, 250, 500, and 1000 µg of CYL-02, respectively. FIG. 2c indicates DCK::UMK and SSTR2 mRNAs expression in tumors before and following gene therapy. Thus, the inventors demonstrate that the intratumoral injection of CYL-02 resulted in successful therapeutic DNA delivery to tumors and long term anticancerous gene expression.

Radiological Findings and Clinical Efficacy

Stable disease by RECIST was observed in 19 patients (95%), two months following gene therapy and gemcitabine treatment. Patients with metastatic disease at the time of diagnosis did not benefit from intratumoral gene therapy as metastases progressed under treatment in 5 out of 7 patients (71%). On the other hand, 11 out of 12 patients (91%) diagnosed with locally advanced disease remained free of metastases at the end of the protocol. The inventors next focused on the potential efficacy of CYL-02 in pancreatic cancer patients with locally advanced disease, as they may better benefit from the intratumoral injection of the gene therapy product. Of the 13 evaluable patients with locally advanced pancreatic cancer, 10 patients had stable disease (SD) as best response. Minor response (MR, defined as −10% to −30% by RECIST) was observed in two patients. Decrease in CA 19-9 (>50%) was observed in six of twelve evaluable patients (FIG. 3). Patient #22 was not evaluable (Lewis A blood group). For metastatic patients (n=7), CA 19-9 levels increased 1.83±1.42 fold. As previous treatments could have influenced the therapeutic outcome in this study, The inventors selected locally advanced patients receiving CYL-02+gemcitabine as a first-line treatment (n=9, Table 1). When analyzed according to the dose of CYL-02 received, no trend was observed in efficacy (median progression-free (PFS) and median overall survival (OS)). All patients were diagnosed with stable disease (n=9), and were further treated with gemcitabine for 4 months after completing the gene therapy program. The PFS and OS rates reached 5.9 (1.8-11.5) and 12.6 (1.8-27.8) months, respectively, in this subgroup of PDAC patients.

Biomarkers Discovery

Figure 4B:
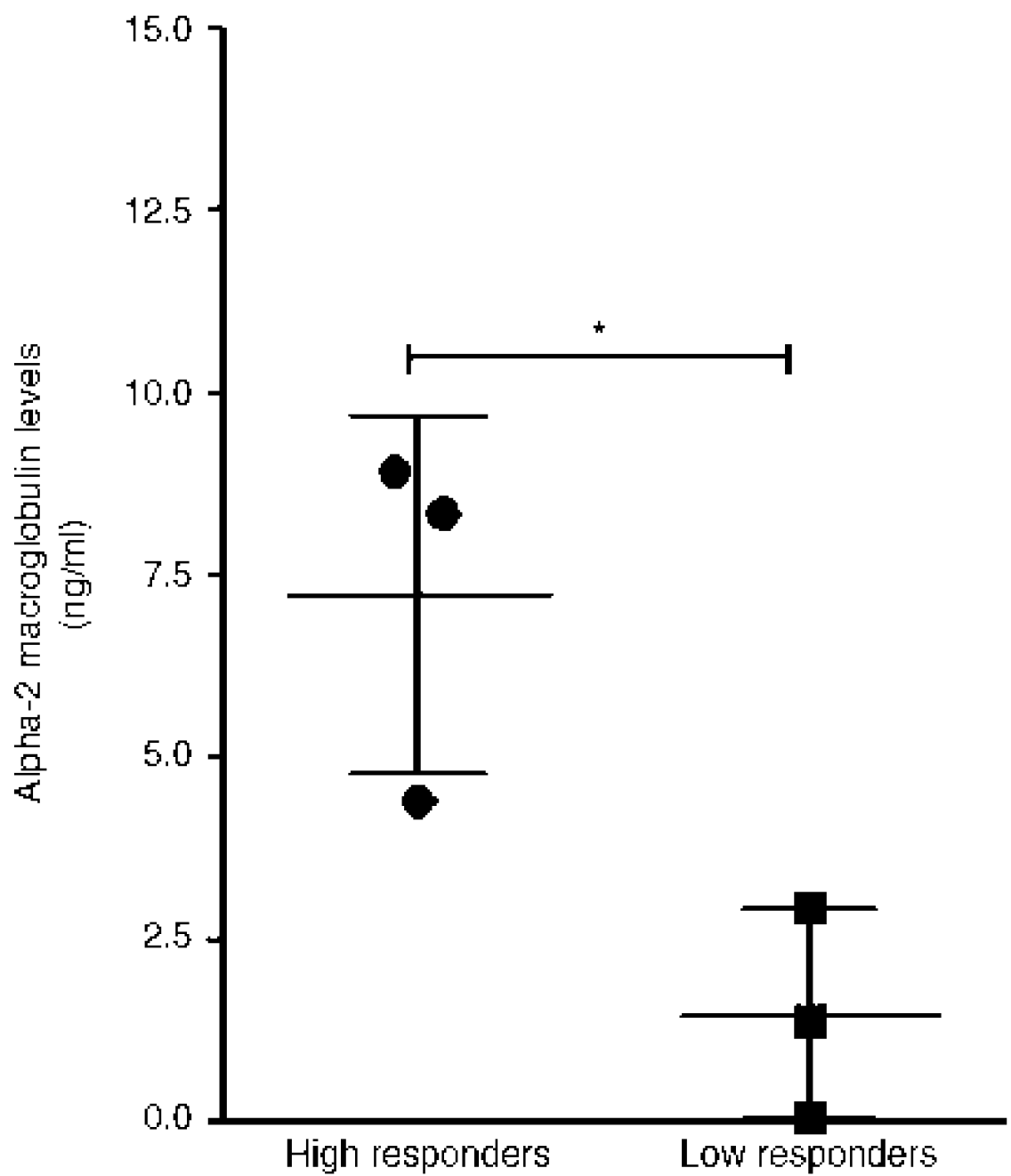
Figure 4C:
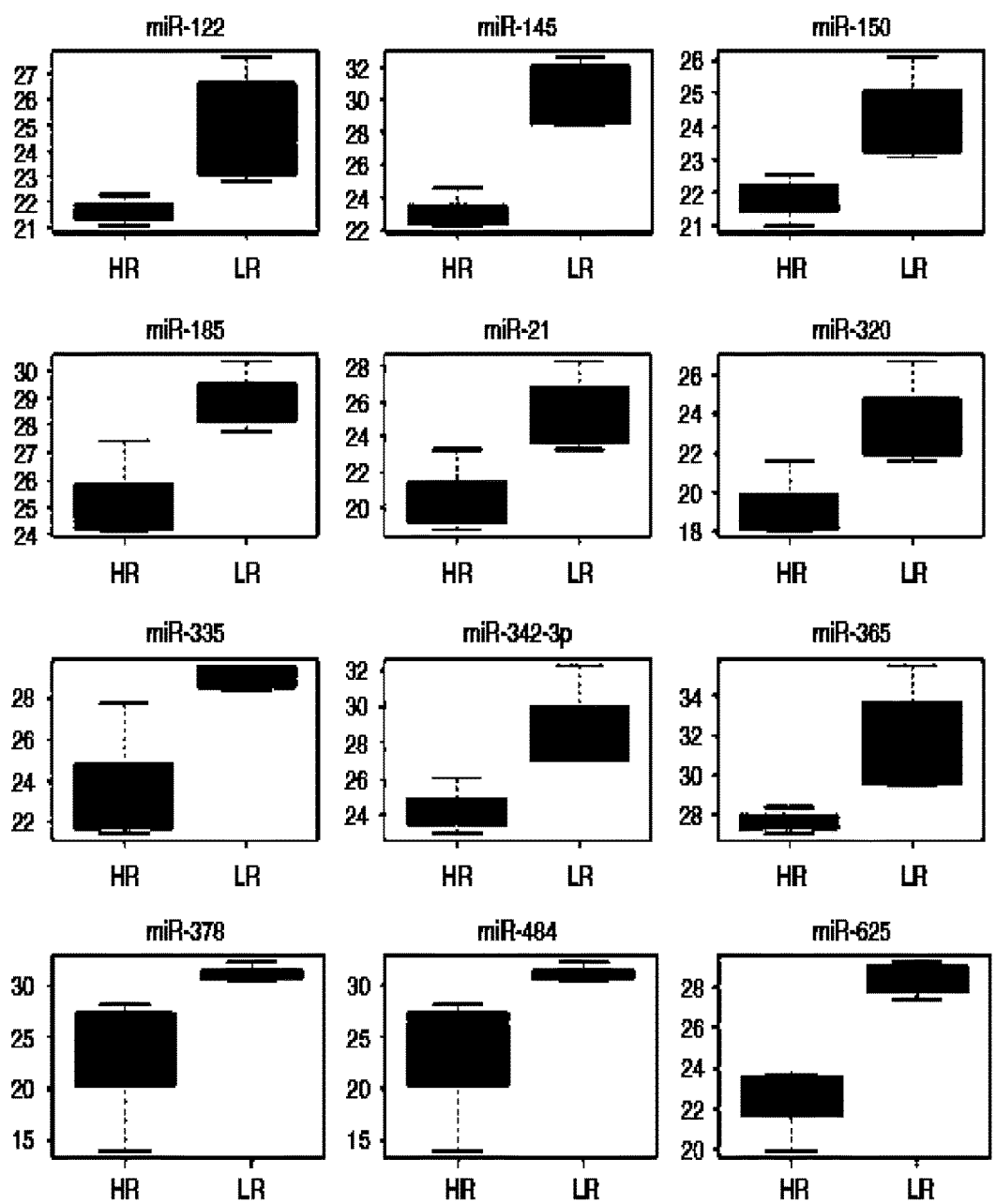

The inventors performed high-throughput proteomic studies from the plasma of patients diagnosed with locally advanced PDAC, before treatment by gene therapy. Six patients were eligible for this study. Proteomic data successfully classified patients in two groups, high responders (patients #6, 9, 12, median PFS=11,1±2.04 months) and low responders, (patients #17, 19, 20, median PFS=4.2±1.52 months) to gene therapy. Interestingly, RECIST analysis 6-months post gene therapy revealed that patients #17, 19 and 20 had progressive disease, while patients #6, 9 and 12 were still stable. The inventors validated that statistical analysis of differences between groups was strictly related to biological parameters. The inventors identified a set of 25 proteins (FIG. 4A and Table 3) with a significant Mascot score (Table 3), that discriminate the two groups of patients and validated that A2MG (α2-macroglobuline) is elevated prior to treatment in patients that will better respond to gene therapy (FIG. 4B). The inventors also identified a set of 12 miRNAs (miR-378, miR-145, miR-150, miR-185, miR-21, miR-484, miR-625, miR-122, miR-320, miR-335, miR-365, and miR-342-3p), that are significantly elevated in the plasma of high responders to treatment (FIG. 4C).

TABLE 3

Proteomic profiling of patients with locally advanced pancreatic cancer treated by gene therapy. The peptides mixtures were analysed by nanoHPLC-chip-MS/MS from the plasma of patients with locally advanced pancreatic cancer and treated by gene therapy (n = 10) as described in Material and Methods. Among the listed proteins, Alpha-2 macroglobuline was identified with a Mascot score = 222 and a number of peptide = 11.

| Accession | Peptide count | Peptides used for quantitation | Confidence score | Anova(p) | Max fold change | Highest mean condition |
|---|---|---|---|---|---|---|
| IGHG4 HUMAN | 4 | 1 | 128.61 | 0.168 | 2.72 | LR |
| K2C1_HUMAN | 1 | 1 | 19.88 | 0.060 | 1.72 | HR |
| A2MG_HUMAN | 11 | 11 | 221.49 | 0.079 | 1.63 | HR |
| APOA1 HUMAN | 3 | 3 | 149.51 | 0.963 | 1.48 | HR |
| FIBG_HUMAN | 18 | 15 | 501.55 | 0.598 | 1.41 | LR |
| AACT_HUMAN | 3 | 2 | 116.79 | 0.268 | 1.39 | LR |
| EXOC2_HUMAN | 2 | 2 | 14.02 | 0.441 | 1.39 | HR |
| TRFE_HUMAN | 5 | 4 | 182.55 | 0.383 | 1.33 | HR |
| C05_HUMAN | 11 | 11 | 203.97 | 0.250 | 1.33 | HR |
| A16L2_HUMAN | 3 | 1 | 40.36 | 0.116 | 1.33 | HR |
| FBLN3 HUMAN | 2 | 2 | 63.62 | 0.302 | 1.31 | HR |
| HR.G_HUMAN | 2 | 2 | 146.6 | 0.173 | 1.30 | LR |
| VTNC_HUMAN | 6 | 5 | 108.11 | 0.467 | 1.30 | HR |

Discussion

Pancreatic cancer is a highly lethal human cancer in which incidence and mortality are almost identical. Reasons for this are 1)—a late diagnosis because pancreatic cancer provides no signs and/or symptoms until the disease has become advanced with metastases and 2)—the lack of curative treatment for advanced disease[17]. Pancreatic cancer has a sophisticated network of biological activities that maintains self-sufficiency in growth signals, is resistant to endogenous antiproliferative signals, evades apoptosis, has limitless replicative potential, and undergoes tissue invasion and metastasis[18,19]. This heterogeneity stems for the unchallenged resistance of pancreatic cancer to conventional therapeutic approaches (chemotherapy, radiotherapy . . . ) and targeted biotherapies. The outlook for patients with advanced pancreatic cancer remains dismal, as these patients are still not cured with conventional therapies, and there remains an urgent need for new approaches, such as gene therapy.

The inventors have devised over the past few years a highly innovative approach based on anticancerous intratumoral gene transfer, which does not rely on a specific genetic and/or cellular background to inhibit the growth of the pancreatic tumors. The inventors designed and produced in this study a plasmid-based gene-therapy product, namely CYL-02. The data presented herein from the preclinical and the phase I studies of CYL-02 support the following conclusions. From preclinical studies, CYL-02 gene therapy combined with gemcitabine treatment strongly inhibits the growth and the metastatic spread of experimental pancreatic tumors. The study concept is based on an experimental preclinical model which shows that the combination of chemosensitizing (DCK and UMK), that demonstrate superior antitumoral activity than either protein alone (unpublished observation), and antitumoral (SSTR2) genes delivered by a non-viral vector (Jet-PEI) with gemcitabine results in the inhibition of cancer cell proliferation of greater magnitude than either agent alone and correlates with superior antitumor responses.

The Phase I clinical study supports that gene therapy, administrated in tumors using EUS, and chemotherapy can be given safely to patients with advanced, treatment refractory pancreatic cancer. This is in marked contrast to many conventional options in which the toxicities can be cumulative, and impairment in quality of life has to be weighed against potential benefit. For example, the 3-drug combination of fluorouracil (5-FU), oxaliplatin and irinotecan (FOLFIRINOX) showed improved survival compared with gemcitabine monotherapy in patients with good performance status, but safety is less favorable[20]. While EUS can eventually lead to several complications[21], injecting CYL-02 in the pancreas didn't induced morbidity, such as severe acute pancreatitis. In addition, the co-administration of CYL-02 with gemcitabine did not significantly potentiate the hematologic impact of gemcitabine alone. The inventors conclude that CYL-02 non-viral gene therapy is safe and tolerable in subjects. The inventors demonstrate a dose-dependent augmentation of systemic and tumoral CYL-02 DNA, with long-term expression of therapeutic mRNAs in tumors. The presence of increasing levels of CYL-02 DNA in the blood suggests systemic leakage of the product in the vasculature or release by necrotic tumor cells. With both biologic and targeted agents, dose selection can be complex as the usual drug development philosophy of using MTD may not be relevant. The maximum dose may not be the most biologically effective dose. While patients receiving the highest dose of CYL-02 had significantly more copies of therapeutic DNA, there does not appear to be a dose-dependent augmentation of therapeutic gene expression in tumors. This may be due to either a greater magnitude of target amplification by q(RT)PCR vs PCR, and/or accelerated RNA degradation in a very hostile tumor microenvironment. Unfortunately, while the inventors demonstrated in experimental models that the gene therapy product could transfect almost one-fourth of the tumor cells, the inventors could not perform immunochemistry to assess the efficacy of gene transfer during the clinical trial because of the paucity of the material collected following fine needle aspiration. The inventors conclude that the RPTD for CYL-02 on days 1 and 28 is 1000 µg when combined with gemcitabine 1000 mg/m² on days 3, 10, 17, 30, 37 and 44.

The inventors are encouraged by the antitumor activity of CYL-02 observed in pancreatic cancer patients, as 19 out of 20 subjects did not progress under treatment (95%), according to RECIST criteria. Interestingly, 12 out of 13 patients with locally advanced PDAC at the time of diagnosis remained free of metastasis following gene therapy (92%). The later finding must be pondered because a subset of patients with locally advanced disease never develops metastatic disease. In locally advanced patients, CA 19-9 cancer marker levels decreased significantly following gene therapy combined to gemcitabine treatment. However, there were no significant differences in the efficacies of different doses groups. On the other hand, CYL-02 treatment failed to impact pre-established, distant metastatic growth. Efficacy was documented both in gemcitabine-naïve and gemcitabine-refractory patients, supporting the notion that CYL-02 targeted gene therapy could sensitize to and/or reverse acquired gemcitabine resistance.

As previous treatments could have influenced the therapeutic outcome in this study, the inventors restrained the survival rate analysis to patients with locally advanced disease receiving CYL-02+gemcitabine as a first-line treatment to evaluate CYL-02 therapeutic activity. The 12.6 months of OS, 5.9 months of PFS and 1-year survival of 66% are longer than that commonly observed with gemcitabine alone[2]. To our knowledge, our study is the first assessment of PEI-based, non viral gene therapy administrated to pancreatic cancer patients with locally-advanced pancreatic cancer. TNFerade (targeted adenoviral vector encoding for TNFα) was tested in phase I/II clinical trial during which clinical efficacy was demonstrated when combined with radio-chemotherapy, while dose-limiting toxicities were identified[22]. However, a recent randomized phase III multi-institutional study demonstrated that TNFerade combined with standard-of-care was safe, but failed to prolong survival in patients with locally-advanced pancreatic cancer, as compared to standard-of-care alone[23]. In another study, naked plasmid DNA encoding for diphtheria-toxin gene was administered intratumorally in subjects with unresectable, locally advanced, non-metastatic pancreatic cancer patients[24]. This small study conducted in six patients showed evidences of safety and limited efficacy. On the other hand, very promising late-phase vaccine studies are currently ongoing for pancreatic cancer treatment. These studies are based on the use of tumor associated antigen-specific cytotoxic T lymphocytes, and were proved to be very efficient in experimental models of pancreatic cancer[25, 26]. It is tempting to speculate that the antitumoral gene therapy approach described herein may complement cell-based therapies by revealing new tumor associated antigen to improve the therapeutic response.

During the THERGAP trial, PFS and OS rates varied widely when locally advanced patients were treated by CYL-02 and gemcitabine (1.8-11.5 and 1.8-27.8 months, respectively), while these patients received the exact same therapeutic regimen, a combination of gene therapy and chemotherapy for two months, followed by gemcitabine alone for four months. In other words, Patients progressed under treatment (i.e. PFS<6 months), while other Patients did not (i.e. PFS>6 months). The identification of any biomarkers that helps refine our therapeutic decision making would be immensely helpful and represents a worthy goal. Gemcitabine requires transporter proteins to cross cell membranes. Low expression of human equilibrative nucleoside transporter-1 (hENT1) may result in gemcitabine resistance in pancreatic cancer. Recent studies have revealed that high levels of hENT1 in pancreatic cancer predict longer survival times in patients treated with adjuvant gemcitabine[14]. In another study, CO-101, a lipid-drug conjugate of gemcitabine, was designed to enter cells independently of hENT1[27]. However, CO-101 was found not superior to gemcitabine in patients with metastatic pancreatic cancer and low tumor hENT1[27]. In addition, metastasis hENT1 expression doesn't predict gemcitabine outcome[27]. In this study, hENT1 mRNA expression at the time of diagnosis didn't predict response to treatment. Thus, the inventors performed blood-based proteomic and miRNA expression studies to identify a set of 25 proteins and 12 miRNAs that predict for response to treatment to gene therapy of patients diagnosed with locally advanced pancreatic cancer.

In summary, CYL-02 plus gemcitabine regimen is well tolerated in patients with advanced pancreatic cancer. There are encouraging evidences of therapeutic gene delivery and expression, and potential clinical benefit with the identification of non-invasive biomarkers for patient selection. Given the favorable safety profile and the encouraging antitumor activity of the CYL-02 plus gemcitabine regimen, a clinical trial comparing gemcitabine plus CYL-02 to gemcitabine alone has initiated in 80 patients.

REFERENCES

Throughout this application, various references describe the state of the art to which this invention pertains. The disclosures of these references are hereby incorporated by reference into the present disclosure.

1. Cancer Facts & Figures 2013 at <http://www.cancer.org/research/cancerfactsfigures/cancerfactsfigures/cancer-facts-figures-2013>.
2. Burris, H A, 3rd, Moore, M J, Andersen, J, Green, M R, Rothenberg, M L, Modiano, M R, et al. (1997). Improvements in survival and clinical benefit with gemcitabine as first-line therapy for patients with advanced pancreas cancer: a randomized trial. J. Clin. Oncol. Off. J. Am. Soc. Clin. Oncol. 15: 2403-2413.
3. Pancreatic Cancer Action Network at <http://www.pancan.org/>.
4. Moore, M J, Goldstein, D, Hamm, J, Figer, A, Hecht, J R, Gallinger, S, et al. (2007). Erlotinib plus gemcitabine compared with gemcitabine alone in patients with advanced pancreatic cancer: a phase III trial of the National Cancer Institute of Canada Clinical Trials Group. J. Clin. Oncol. Off. J. Am. Soc. Clin. Oncol. 25: 1960-1966.
5. Von Hoff, D D, Ervin, T, Arena, F P, Chiorean, E G, Infante, J, Moore, M, et al. (2013). Increased survival in pancreatic cancer with nab-paclitaxel plus gemcitabine. N. Engl. J. Med. 369: 1691-1703.
6. Buscail, L, Saint-Laurent, N, Chastre, E, Vaillant, J C, Gespach, C, Capella, G, et al. (1996). Loss of sst2 somatostatin receptor gene expression in human pancreatic and colorectal cancer. Cancer Res. 56: 1823-1827.
7. Carrere, N, Vernejoul, F, Souque, A, Asnacios, A, Vaysse, N, Pradayrol, L, et al. (2005). Characterization of the bystander effect of somatostatin receptor sst2 after in vivo gene transfer into human pancreatic cancer cells. Hum. Gene Ther. 16: 1175-1193.
8. Vernejoul, F, Faure, P, Benali, N, Calise, D, Tiraby, G, Pradayrol, L, et al. (2002). Antitumor effect of in vivo somatostatin receptor subtype 2 gene transfer in primary and metastatic pancreatic cancer models. Cancer Res. 62: 6124-6131.
9. Rochaix, P, Delesque, N, Esteve, J P, Saint-Laurent, N, Voight, J J, Vaysse, N, et al. (1999). Gene therapy for pancreatic carcinoma: local and distant antitumor effects after somatostatin receptor sst2 gene transfer. Hum. Gene Ther. 10: 995-1008.
10. Cordelier, P, Bienvenu, C, Lulka, H, Marrache, F, Bouisson, M, Openheim, A, et al. (2007). Replication-deficient rSV40 mediate pancreatic gene transfer and long-term inhibition of tumor growth. Cancer Gene Ther. 14: 19-29.
11. Delesque, N, Buscail, L, Esteve, J P, Saint-Laurent, N, Müller, C, Weckbecker, G, et al. (1997). sst2 somatostatin receptor expression reverses tumorigenicity of human pancreatic cancer cells. Cancer Res. 57: 956-962.
12. Guillermet, J, Saint-Laurent, N, Rochaix, P, Cuvillier, O, Levade, T, Schally, A V, et al. (2003). Somatostatin receptor subtype 2 sensitizes human pancreatic cancer cells to death ligand-induced apoptosis. Proc. Natl. Acad. Sci. U.S.A. 100: 155-160.
13. Ohhashi, S, Ohuchida, K, Mizumoto, K, Fujita, H, Egami, T, Yu, J, et al. (2008). Down-regulation of Deoxycytidine Kinase Enhances Acquired Resistance to Gemcitabine in Pancreatic Cancer. Anticancer Res. 28: 2205-2212.
14. Maréchal, R, Bachet, J-B, Mackey, J R, Dalban, C, Demetter, P, Graham, K, et al. (2012). Levels of gemcitabine transport and metabolism proteins predict survival times of patients treated with gemcitabine for pancreatic adenocarcinoma. Gastroenterology 143: 664-674.e1-6.
15. Vernejoul, F, Ghénassia, L, Souque, A, Lulka, H, Drocourt, D, Cordelier, P, et al. (2006). Gene therapy based on gemcitabine chemosensitization suppresses pancreatic tumor growth. Mol. Ther. J. Am. Soc. Gene Ther. 14: 758-767.
16. Schultz, N A, Dehlendorff, C, Jensen, B V, Bjerregaard, J K, Nielsen, K R, Bojesen, S E, et al. (2014). MicroRNA biomarkers in whole blood for detection of pancreatic cancer. JAMA J. Am. Med. Assoc. 311: 392-404.
17. Siegel, R, Naishadham, D and Jemal, A (2013). Cancer statistics, 2013. CA. Cancer J. Clin. 63: 11-30.
18. Yachida, S, Jones, S, Bozic, I, Antal, T, Leary, R, Fu, B J, et al. (2010). Distant metastasis occurs late during the genetic evolution of pancreatic cancer. Nature 467: 1114-U126.
19. Jones, S, Zhang, X S, Parsons, D W, Lin, J C H, Leary, R J, Angenendt, P, et al. (2008). Core signaling pathways in human pancreatic cancers revealed by global genomic analyses. Science 321: 1801-1806.
20. Gourgou-Bourgade, S, Bascoul-Mollevi, C, Desseigne, F, Ychou, M, Bouché, O, Guimbaud, R, et al. (2013). Impact of FOLFIRINOX compared with gemcitabine on quality of life in patients with metastatic pancreatic cancer: results from the PRODIGE 4/ACCORD 11 randomized trial. J. Clin. Oncol. Off. J. Am. Soc. Clin. Oncol. 31: 23-29.
21. Bournet, B, Migueres, I, Delacroix, M, Vigouroux, D, Bornet, J-L, Escourrou, J, et al. (2006). Early morbidity of endoscopic ultrasound: 13 years' experience at a referral center. Endoscopy 38: 349-354.
22. Hecht, J R, Farrell, J J, Senzer, N, Nemunaitis, J, Rosemurgy, A, Chung, T, et al. (2012). EUS or percutaneously guided intratumoral TNFerade biologic with 5-fluorouracil and radiotherapy for first-line treatment of locally advanced pancreatic cancer: a phase I/II study. Gastrointest. Endosc. 75: 332-338.
23. Herman, J M, Wild, A T, Wang, H, Tran, P T, Chang, K J, Taylor, G E, et al. (2013). Randomized phase III multi-institutional study of TNFerade biologic with fluorouracil and radiotherapy for locally advanced pancreatic cancer: final results. J. Clin. Oncol. Off. J. Am. Soc. Clin. Oncol. 31: 886-894.
24. Hanna, N, Ohana, P, Konikoff, F M, Leichtmann, G, Hubert, A, Appelbaum, L, et al. (2012). Phase ½a, dose-escalation, safety, pharmacokinetic and preliminary efficacy study of intratumoral administration of BC-819 in patients with unresectable pancreatic cancer. Cancer Gene Ther. 19: 374-381.
25. Anurathapan, U, Chan, R C, Hindi, H F, Mucharla, R, Bajgain, P, Hayes, B C, et al. (2014). Kinetics of tumor destruction by chimeric antigen receptor-modified T cells. Mol. Ther. J. Am. Soc. Gene Ther. 22: 623-633.
26. Chmielewski, M, Hahn, O, Rappl, G, Nowak, M, Schmidt-Wolf, I H, Hombach, A A, et al. (2012). T cells that target carcinoembryonic antigen eradicate orthotopic pancreatic carcinomas without inducing autoimmune colitis in mice. Gastroenterology 143: 1095-1107.e2.
27. Poplin, E, Wasan, H, Rolfe, L, Raponi, M, Ikdahl, T, Bondarenko, I, et al. (2013). Randomized, multicenter, phase II study of CO-101 versus gemcitabine in patients with metastatic pancreatic ductal adenocarcinoma: including a prospective evaluation of the role of hENT1 in gemcitabine or CO-101 sensitivity. J. Clin. Oncol. Off. J. Am. Soc. Clin. Oncol. 31: 4453-4461.
28. Benali, N, Cordelier, P, Calise, D, Pages, P, Rochaix, P, Nagy, A, et al. (2000). Inhibition of growth and metastatic progression of pancreatic carcinoma in hamster after somatostatin receptor subtype 2 (sst2) gene expression and administration of cytotoxic somatostatin analog AN-238. Proc. Natl. Acad. Sci. U.S.A. 97: 9180-9185.
29. Chang, S C, Erwin, A E and Lee, A S (1989). Glucose-regulated protein (GRP94 and GRP78) genes share common regulatory domains and are coordinately regulated by common trans-acting factors. Mol. Cell. Biol. 9: 2153-2162.
30. Al Saati, T, Clerc, P, Hanoun, N, Peuget, S, Lulka, H, Gigoux, V, et al. (2013). Oxidative stress induced by inactivation of TP53INP1 cooperates with KrasG12D to initiate and promote pancreatic carcinogenesis in the murine pancreas. Am. J. Pathol. 182: 1996-2004.
31. Cancer Facts & Figures 2013 [Internet]. [cited 2014 Feb. 10]; Available from: http://www.cancer.org/research/cancerfactsfigures/cancerfactsfigures/cancer-facts-figures-2013
32. Burris H A 3rd, Moore M J, Andersen J, Green M R, Rothenberg M L, Modiano M R, Cripps M C, Portenoy R K, Storniolo A M, Tarassoff P, Nelson R, Don F A, Stephens C D, Von Hoff D D. Improvements in survival and clinical benefit with gemcitabine as first-line therapy for patients with advanced pancreas cancer: a randomized trial. J Clin Oncol Off J Am Soc Clin Oncol 1997; 15:2403-13 [PMID: 9196156]
33. Pancreatic Cancer Action Network [Internet]. Available from: http://www.pancan.org/
34. Humeau M, Torrisani J, Cordelier P. miRNA in clinical practice: Pancreatic cancer. Clin Biochem 2013; [PMID: 23570860 DOI: 10.1016/j.clinbiochem.2013.03.019]
35. Ryan D P1, Hong T S, Bardeesy N. Pancreatic adenocarcinoma. N Engl J Med. 2014 Sep. 11; 371(11):1039-49 [doi: 10.1056/NEJMra1404198].
36. Borth W. Alpha 2-macroglobulin, a multifunctional binding protein with targeting characteristics. FASEB J. 1992 December; 6(15):3345-53.
37. Borth W. Alpha 2-macroglobulin. A multifunctional binding and targeting protein with possible roles in immunity and autoimmunity. Ann N Y Acad Sci. 1994 Sep. 10; 737:267-72.

The invention claimed is:
1. A method for chemosensitization of advanced pancreatic cancer in a subject in need thereof comprising the steps of:
   a) determining whether a subject afflicted with advanced pancreatic cancer will be a responder to a gene therapy and gemcitabine combination treatment by
      i) measuring the expression level of at least one biomarker selected from A2MG, K2C1, APOA1, EXOC2, TRFE, CO5, A16L2, FBLN3, VTNC, IGHG4, FIBG, AACT, HRG, KING1, FETUA, PLMN, THRB, KLBK1, APOH, FHR5, M3K19, CLUS, PROS, C4BP4, FIBB, miR-378, miR-145, miR-150, miR-185, miR-21, miR-484, miR-625, miR-122, miR-320, miR-335, miR-365 and miR-342-3p in a blood sample obtained from said subject before the treatment,
      ii) comparing the expression level measured in step i) with a corresponding reference value derived from subjects who are non-responders to the treatment; and
      iii) determining that the subject is a responder when
         the expression level of one or more of A2MG, K2C1, APOA1, EXOC2, TRFE, CO5, A16L2, FBLN3, VTNC, miR-378, miR-145, miR-150, miR-185, miR-21, miR-484, miR-625, miR-122, miR-320, miR-335, miR-365 and miR-342-3p is higher than the reference value; and/or
         the expression level of one or more of IGHG4, FIBG, AACT, HRG, KING1, FETUA, PLMN, THRB, KLBK1, APOH, FHR5, M3K19, CLUS, PROS, C4BP4, and FIBB is lower than the reference value; and
   b) administering the gene therapy and gemcitabine combination treatment to said subject determined to be a responder, thereby chemosensitizing the subject.
2. The method of claim 1, wherein a plurality of the biomarkers are measured in step i).

* * * * *